US011130889B2

(12) United States Patent
Richter et al.

(10) Patent No.: US 11,130,889 B2
(45) Date of Patent: Sep. 28, 2021

(54) POST-CURABLE PRESSURE-SENSITIVE ADHESIVE

(71) Applicant: 3M INNOVATIVE PROPERTIES COMPANY, St. Paul, MN (US)

(72) Inventors: Mareike Richter, Dusseldorf (DE); Kerstin Unverhau, Neuss (DE); Silke D. Mechernich, Neuss (DE); Siegfried R. Goeb, Willich (DE); Peter Bissinger, Diessen (DE)

(73) Assignee: 3M Innovative Properties Company, St. Paul, MN (US)

( * ) Notice: Subject to any disclaimer, the term of this patent is extended or adjusted under 35 U.S.C. 154(b) by 181 days.

(21) Appl. No.: 16/358,095

(22) Filed: Mar. 19, 2019

(65) Prior Publication Data

US 2019/0211236 A1 Jul. 11, 2019

Related U.S. Application Data

(63) Continuation of application No. 15/102,824, filed as application No. PCT/US2014/068723 on Dec. 5, 2014, now abandoned.

(30) Foreign Application Priority Data

Dec. 18, 2013 (EP) ..................... 13198136

(51) Int. Cl.
| | | |
|---|---|---|
| *C09J 11/08* | (2006.01) | |
| *C07D 203/08* | (2006.01) | |
| *C09J 4/06* | (2006.01) | |
| *C09J 5/00* | (2006.01) | |
| *C09J 9/00* | (2006.01) | |
| *C09J 133/08* | (2006.01) | |
| *C08F 220/18* | (2006.01) | |
| *C09J 4/00* | (2006.01) | |

(52) U.S. Cl.
CPC ............ *C09J 11/08* (2013.01); *C07D 203/08* (2013.01); *C09J 4/06* (2013.01); *C09J 5/00* (2013.01); *C09J 9/00* (2013.01); *C09J 133/08* (2013.01); *C08F 220/18* (2013.01); *C09J 4/00* (2013.01); *C09J 2301/302* (2020.08); *C09J 2433/00* (2013.01); *C09J 2479/02* (2013.01)

(58) Field of Classification Search
CPC ....... C09J 11/08; C09J 4/06; C09J 5/00; C09J 9/00; C09J 133/08; C09J 2301/302; C09J 4/00; C09J 2433/00; C09J 2479/02; C07D 203/08; C08F 220/18
See application file for complete search history.

(56) References Cited

U.S. PATENT DOCUMENTS

| | | |
|---|---|---|
| 4,415,615 A | 11/1983 | Esmay |
| 5,089,536 A | 2/1992 | Palazzotto |
| 5,506,279 A | 4/1996 | Babu |
| 5,721,289 A | 2/1998 | Karim |
| 5,902,836 A | 5/1999 | Bennett |
| 2004/0127594 A1 | 7/2004 | Yang |
| 2007/0213429 A1 | 9/2007 | Cheng |
| 2008/0032231 A1 | 2/2008 | Hatakeyama |
| 2008/0200587 A1 | 8/2008 | Filiatrault |
| 2008/0318167 A1 | 12/2008 | Kim |
| 2009/0105437 A1 | 4/2009 | Determan |
| 2010/0227969 A1 | 9/2010 | Zhu |
| 2011/0076493 A1 | 3/2011 | Kavanagh |
| 2011/0152445 A1 | 6/2011 | Krepski |
| 2011/0178248 A1 | 7/2011 | Kavanagh |
| 2012/0171484 A1 | 7/2012 | Ko |
| 2013/0196152 A1 | 8/2013 | Mahoney |
| 2016/0312080 A1 | 10/2016 | Richter |
| 2017/0355885 A1 | 12/2017 | Mechernich |

FOREIGN PATENT DOCUMENTS

| | | |
|---|---|---|
| CN | 101880352 | 11/2010 |
| EP | 0798354 | 10/1997 |
| EP | 2368953 | 9/2011 |
| JP | 2002-097439 | 4/2002 |
| KR | 2011-0003062 | 1/2011 |
| TW | 201339272 | 10/2013 |
| WO | WO 2004/009720 | 1/2004 |
| WO | WO 2009/152126 | 12/2009 |
| WO | WO 2012/033633 | 3/2012 |

OTHER PUBLICATIONS

International Search Report for PCT International Application No. PCT/US2014/068723, dated Jan. 28, 2015, 4 pages.
European Search Report for EP Application No. 13198136.7, date of completion of the search, dated May 26, 2014 (6 pages).
King, "Solutions for Coatings, Inks, Adhesives, Elastomers, and Sealants", King Industries, (2012).

*Primary Examiner* — Robert S Walters, Jr.
(74) *Attorney, Agent, or Firm* — Jean A. Lown

(57) ABSTRACT

The present disclosure is directed to a curable precursor of a pressure sensitive adhesive comprising:
  a) a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
  b) a polyfunctional aziridine curing agent; and
  c) an acid generating agent.
The present disclosure is also directed to a method of manufacturing such pressure sensitive adhesives and uses thereof.

9 Claims, No Drawings

POST-CURABLE PRESSURE-SENSITIVE ADHESIVE

CROSS REFERENCE TO RELATED APPLICATIONS

This application is a continuation application of pending prior application Ser. No. 15/102,824, filed Jun. 8, 2016, which is a 371 of International Application No. PCT/US2014/068723, filed Dec. 5, 2014, which claims priority to European Application No. EP 13198136.7, filed Dec. 18, 2013.

TECHNICAL FIELD

The present disclosure relates generally to the field of adhesives, more specifically to the field of pressure sensitive adhesive (PSA). The present disclosure also relates to a method of manufacturing such pressure sensitive adhesives and uses thereof.

BACKGROUND

Adhesives have been used for a variety of marking, holding, protecting, sealing and masking purposes. Adhesive tapes generally comprise a backing, or substrate, and an adhesive. One type of adhesive which is particularly preferred for many applications is represented by pressure sensitive adhesives.

Pressure-sensitive tapes are virtually ubiquitous in the home and workplace. In its simplest configuration, a pressure-sensitive tape comprises an adhesive and a backing, and the overall construction is tacky at the use temperature and adheres to a variety of substrates using only moderate pressure to form the bond. In this fashion, pressure-sensitive tapes constitute a complete, self-contained bonding system.

Pressure sensitive adhesives (PSAs) are well known to one of ordinary skill in the art, and according to the Pressure-Sensitive Tape Council, PSAs are known to possess properties including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as PSAs include polymers designed and formulated to exhibit the requisite viscoelastic properties resulting in a desired balance of tack, peel adhesion, and shear holding power. PSAs are characterized by being normally tacky at room temperature (e.g., 20° C.). PSAs do not embrace compositions merely because they are sticky or adhere to a surface.

These requirements are assessed generally by means of tests which are designed to individually measure tack, adhesion (peel strength), and cohesion (shear holding power), as noted in A. V. Pocius in Adhesion and Adhesives Technology: An Introduction, $2^{nd}$ Ed., Hanser Gardner Publication, Cincinnati, Ohio, 2002. These measurements taken together constitute the balance of properties often used to characterize a PSA.

With broadened use of pressure-sensitive tapes over the years, performance requirements have become more demanding. Shear holding capability, for example, which originally was intended for applications supporting modest loads at room temperature, has now increased substantially for many applications in terms of operating temperature and load. When used as attachment devices for a variety of assembly and manufacturing applications, such as interior or exterior automotive mounting of panels and molding, or in the construction industry, pressure sensitive adhesives are additionally required to provide good adhesion performance to rough or irregular surfaces. In addition, many applications require pressure sensitive adhesives to support a load at elevated temperatures, typically in the range of from 70° C. to 90° C., for which high cohesive strengths are required. So-called high performance pressure-sensitive tapes are those capable of supporting loads at elevated temperatures for 10,000 minutes. Increased shear holding capability has generally been accomplished by crosslinking the PSA, although considerable care must be exercised so that high levels of tack and adhesion are retained in order to retain the aforementioned balance of properties.

It is therefore a recognized challenge in the adhesive tapes industry to combine good adhesion and good cohesion properties. In order to optimize the adhesion of a PSA to a particular substrate, in particular an irregular substrate, an excellent surface wetting is necessary.

Partial solutions have been described in the art, whereby a non- or very low crosslinked adhesive is applied to a surface and then post-cured, so that, after an adequate surface wetting, the cohesive strength can be built up. In that context, the so-called "semi-structural tapes" described e.g. in U.S. Pat. No. 5,721,289 (Karim et al.) have been used, as. These systems are based on post-curable epoxy functionalities and specifically require using a superacid which is activated by UV irradiation as triggering energy. However, these known systems show undesired moisture sensitivity as the superacid needed for UV-induced cationic curing or crosslinking of the epoxy functionalities decomposes to hydronium ion, rendering ineffective the ring-opening polymerization of epoxies. Other known post-curable systems are based on the so-called "DICY-chemistry" described e.g. in EP-A1-0798354, wherein an epoxy-amine curing reaction is triggered with heat. However, these systems require a continuous heating step so as to maintain the curing reaction until the curing or crosslinking step has been completed. Patent applications US 2011/0076493-A1 (Kavanagh et al.) and US 2011/0178248-A1 (Kavanagh et al.) disclose pre-adhesive compositions comprising an aziridine crosslinking agent.

The commonly known curing or crosslinking systems do not often provide industrially viable solutions for the production of pressure sensitive adhesives having acceptable characteristics. Without contesting the technical advantages associated with the curing or crosslinking systems known in the art for producing pressure sensitive adhesives, there is still a need for a pressure sensitive adhesive provided with an excellent and versatile balance of adhesive and cohesive properties, in particular on uneven or irregular substrates.

Other advantages of the pressure sensitive adhesives and methods of the invention will be apparent from the following description.

SUMMARY

According to one aspect, the present disclosure relates to a curable precursor of a pressure sensitive adhesive comprising:
  a) a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
  b) a polyfunctional aziridine curing agent; and
  c) an acid generating agent.

In another aspect, the present disclosure relates to a composite assembly comprising a substrate and a curable precursor of a pressure sensitive adhesive as above described applied onto at least part of the surface of the substrate, thereby forming a layer of a curable precursor of a pressure sensitive adhesive.

According to still another aspect of the present disclosure, it is provided a method of applying a pressure sensitive adhesive to a substrate, comprising the steps of:
a) providing a curable precursor of a pressure sensitive adhesive comprising:
   i. a (co)polymeric material comprising the reaction product of a (co)polymerizable material comprising a (meth)acrylic acid ester monomer; and optionally, a co-monomer having an ethylenically unsaturated group and which is different from the (meth)acrylate ester monomer;
   ii. a polyfunctional aziridine curing agent; and
   iii. optionally, an acid generating agent;
b) applying the curable precursor of a pressure sensitive adhesive to at least part of the surface of the substrate; and
c) curing the curable precursor of a pressure sensitive adhesive by allowing acid to be released into it.

In still another aspect, the present disclosure relates to the use of a curable precursor of a pressure sensitive adhesive as above-described, for the bonding to an uneven or irregular substrate. In yet another aspect, the present disclosure relates to the use of a curable precursor of a pressure sensitive adhesive, for industrial applications, in particular for automotive applications, in particular for taped seal on body applications.

DETAILED DESCRIPTION

According to a first aspect, the present disclosure relates to a curable precursor of a pressure sensitive adhesive comprising:
a) a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
b) a polyfunctional aziridine curing agent; and
c) an acid generating agent.

In the context of the present disclosure, it has surprisingly been found that a curable precursor of a pressure sensitive adhesive as described above is outstandingly suitable for producing post-cured pressure sensitive adhesives provided with an excellent and versatile balance of adhesive and cohesive properties, in particular on uneven or irregular substrates. The curable precursor of a pressure sensitive adhesive according to the disclosure is particularly suitable to perform on-demand post-curing, i.e. activatable and delayed in-place curing. In the context of the present disclosure, the acid generating agent for use herein acts as an activatable latent source of acid catalysts for cationic (ring-opening) polymerization of the polyfunctional aziridine curing agent, resulting in curing of the precursor of a pressure sensitive adhesive according to the disclosure.

Without wishing to be bound by theory, it is believed that the curing mechanism used to build up inner strength of the pressure sensitive adhesive involves the formation of an interpenetrating network involving the (meth)acrylate ester based (co)polymeric material and an aziridine network resulting from acid-catalyzed cationic ring-opening polymerization of polyfunctional aziridine monomeric units.

Still without wishing to be bound by theory, it is believed that the particular combination of a polyfunctional aziridine curing agent and an acid generating agent, allows providing an excellent surface wetting characteristics to the precursor of a pressure sensitive adhesive on its uncured state, in particular on uneven or irregular substrates, which ultimately translates into providing excellent adhesives and cohesive properties to the pressure sensitive adhesive resulting from the curing of the precursor of the pressure sensitive adhesive.

The curable precursor of a pressure sensitive adhesive of the present disclosure may be (pre)polymerized and cured in-place to produce a pressure sensitive adhesive provided with excellent characteristics directly on the desired substrate or article.

The use of the curable precursor composition and method of the present disclosure affords a number of advantages as compared to conventional post-curable compositions, such as e.g. those based on post-curable epoxy functionalities or on the so-called "DICY-chemistry". These advantages include, but are not limited to, insensitivity of the curable composition to moisture, and ability to perform post-curing of the curable precursor by short initiation with a suitable triggering energy (e.g. thermal energy or actinic radiation) without the necessity to provide a continuous source of triggering energy until the curing is completed.

In addition, the cured pressure sensitive adhesives exhibit high peel strength, high cohesive strength, high temperature shear strength, and excellent stress relaxation properties. The pressure-sensitive adhesives according to the present disclosure, i.e. in the cured state, provide the desired balance of tack, peel adhesion, and shear holding power, and further conform to the Dahlquist criteria; i.e. the modulus of the adhesive at the application temperature, typically room temperature, is less than $3\times106$ dynes/cm at a frequency of 1 Hz.

The pressure sensitive adhesives according to the disclosure may find particular use for adhering e.g. automotive body side mouldings, weather strips, road signs, commercial signs, constructions, electrical cabinets, shell moulds, machine parts, junction boxes or backsheet solutions for photovoltaic modules. In a particular advantageous aspect, the pressure sensitive adhesives of the present disclosure provide excellent adhesion properties on low surface energy substrates, such as polyolefin surfaces and clear coat surfaces. More particularly, the pressure sensitive adhesives disclosed herein may be advantageously bonded to automotive clear coat surfaces.

In the context of the present disclosure, the expression "low surface energy substrates" is meant to refer to those substrates having a surface energy of less than 34 dynes per centimeter. Included among such materials are polypropylene, polyethylene (e.g., high density polyethylene or HDPE), and blends of polypropylene (e.g. PP/EPDM, TPO). The surface energy is typically determined from contact angle measurements as described, for example, in ASTM D7490-08.

In the context of the present disclosure, the term "curing" is not meant to designate crosslinking, but is rather meant to refer to the formation of an interpenetrating polymer network structure, e.g. the interpenetrating network involving the (meth)acrylate ester based (co)polymeric network and the aziridine polymeric network resulting from acid-catalyzed cationic ring-opening polymerization of polyfunctional aziridine monomeric units.

In the context of the present disclosure, and as well known to those skilled in the art, the term "acid generating agent" is meant to refer to a latent source of acid catalysts for performing e.g. cationic (ring-opening) polymerization, and which is activatable by exposure to a suitable triggering energy (such as e.g. thermal energy or actinic radiation).

As used herein, the term "alkyl (meth)acrylate" and "alkyl (meth)acrylate ester" are used interchangeably. The term "(meth)acrylate" refers to an acrylate, methacrylate, or both. The term "(meth)acrylic" refers to methacrylic, acrylic, or both. A (meth)acrylic-based" material refers to one prepared from one or more monomers having a (meth)acryloyl group, which is a group of formula $CH_2=C(R)-(CO)-$ where R is hydrogen or methyl.

The term "alkyl" refers to a monovalent group which is a saturated hydrocarbon. The alkyl can be linear, branched, cyclic, or combinations thereof and typically has 1 to 32 carbon atoms. In some embodiments, the alkyl group contains 1 to 25, 1 to 20, 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, 2-ethylhexyl, 2-octyl and 2-propylheptyl.

The terms "glass transition temperature" and "Tg" are used interchangeably and refer to the glass transition temperature of a material or a mixture. Unless otherwise indicated, glass transition temperature values are determined by Differential Scanning Calorimetry (DSC).

As used herein, the term "heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent.

As used herein, "aryl" is an aromatic group containing 6-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

As used herein, "(hetero)hydrocarbyl" is inclusive of hydrocarbyl alkyl and aryl groups, and heterohydrocarbyl heteroalkyl and heteroaryl groups, the later comprising one or more catenary oxygen heteroatoms such as ether or amino groups. Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supra.

In a typical aspect, the (co)polymeric material comprising the reaction product of a (co)polymerizable material comprising a (meth)acrylate ester monomer, comprises a polymer base material selected from the group consisting of polyacrylates whose main monomer component comprises a linear or branched alkyl (meth)acrylate ester, preferably a non-polar linear or branched alkyl (meth)acrylate ester having a linear or branched alkyl group comprising preferably from 1 to 32, from 1 to 20, or even from 1 to 15 carbon atoms.

According to a particular aspect, the (co)polymeric material for use herein comprises a polymer base material selected from the group consisting of polyacrylates whose main monomer component preferably comprises a linear or branched alkyl (meth)acrylate ester, preferably a non-polar linear or branched alkyl (meth)acrylate ester having a linear or branched alkyl group comprising preferably from 1 to 32, from 1 to 20, or even from 1 to 15 carbon atoms.

According to a preferred aspect of the curable precursor of a pressure sensitive adhesive of the present disclosure, the (co)polymeric material for use herein comprises a polymer base material selected from the group consisting of polyacrylates whose main monomer component comprises a linear or branched alkyl (meth)acrylate ester selected from the group consisting of methyl (meth)acrylate, ethyl (meth)acrylate, n-propyl (meth)acrylate, isopropyl (meth)acrylate, n-butyl acrylate, isobutyl acrylate, tert-butyl (meth)acrylate, n-pentyl (meth)acrylate, iso-pentyl (meth)acrylate, n-hexyl (meth)acrylate, iso-hexyl (meth)acrylate, cyclohexyl (meth)acrylate, phenyl (meth)acrylate, octyl (meth)acrylate, iso-octyl (meth)acrylate, 2-octyl (meth)acrylate, 2-ethylhexyl (meth)acrylate, decyl (meth)acrylate, lauryl (meth)acrylate, 2-propylheptyl (meth)acrylate, stearyl (meth)acrylate, isobornyl acrylate, benzyl (meth)acrylate, octadecyl acrylate, nonyl acrylate, dodecyl acrylate, isophoryl (meth)acrylate, and any combinations or mixtures thereof.

In a more preferred aspect, the linear or branched alkyl (meth)acrylate ester for use herein is selected from the group consisting of iso-octyl (meth)acrylate, 2-ethylhexyl (meth)acrylate, 2-propylheptyl (meth)acrylate, 2-octyl (meth)acrylate, butyl acrylate, and any combinations or mixtures thereof, more preferably from the group consisting of iso-octyl acrylate (IOA), 2-ethylhexyl acrylate (2-EHA), 2-octyl acrylate (2-OA) and 2-propylheptyl acrylate (2-PHA). In a particularly preferred aspect, the linear or branched alkyl (meth)acrylate ester for use herein comprises or consists of 2-ethylhexyl acrylate.

According to an alternative aspect, the linear or branched alkyl (meth)acrylate ester for use herein is selected to comprise 2-octyl(meth)acrylate. Polymer base material derived from 2-octyl (meth)acrylate provides comparable adhesive properties when compared with other isomers of octyl (meth)acrylate, such as n-octyl and isooctyl. Further, the pressure sensitive adhesive compositions have lower inherent and solution viscosities when compared to adhesive compositions derived from other octyl isomers, such as isooctyl acrylate, at the same concentrations, and under the same polymerization conditions.

The 2-octyl (meth)acrylate may be prepared by conventional techniques from 2-octanol and (meth)acryloyl derivates such as esters, acids and acyl halides. The 2-octanol may be prepared by treatment of ricinoleic acid, derived from castor oil, (or ester or acyl halide thereof) with sodium hydroxide, followed by distillation from the co-product sebacic acid.

It is however preferred that the 2-octyl(meth)acrylate monomer for use herein is at least partly, preferably completely (i.e. 100 wt %) derived from biological material, more preferably from a plant material. This may advantageously be used to provide adhesive films/tapes which are at least partly derived from "green" sources, which is ecologically more sustainable and also reduces the dependency on mineral oil and the price development.

In the context of the present disclosure, the term "derived from biological material" is meant to express that from a certain chemical ingredient, at least a part of its chemical structure comes from biological materials, preferably at least 50 wt % of its structure. This definition is in principle the same as for bio-diesel fuel, in which usually only the fatty acid part originates from biological sources whereas the methanol may also be derived from fossil material like coal or mineral oil.

Accordingly, in one specific aspect, at least 50 wt %, at least 75 wt %, or even 100 wt % of the chemical structure of the 2-octyl(meth)acrylate is at least partly, preferably completely (i.e. 100 wt %) derived from biological material, more preferably from a plant material.

The (meth)acrylate ester monomer(s) for use herein may be present in the (co)polymerizable material, in any suitable amounts. In some exemplary aspects, the (meth)acrylate ester monomer(s) are present in amounts up to 100 parts by weight, up to 90 parts by weight, or even up to 80 parts by weight of the (co)polymerizable material. In some other exemplary aspects, this amount is typically of at least 50 parts by weight, or at least 60 parts by weight of the (co)polymerizable material.

Accordingly, in some exemplary aspects, the (meth)acrylate ester monomer(s) are present in amounts in a range of from 50 to 100 parts, from 60 to 95 parts by weight, from 65 to 90 parts, or even from 65 to 80 parts by weight of the (co)polymerizable material.

According to a particular aspect, the (co)polymeric material for use herein may further comprise an optional co-monomer having an ethylenically unsaturated group and which is different from the (meth)acrylate ester monomer(s) described above. Suitable co-monomer(s) having an ethylenically unsaturated group for use herein will be easily identified by those skilled in the art, in the light of the present description. As such, co-monomer(s) having an ethylenically unsaturated group for use herein are not particularly limited as long as they are different from the (meth)acrylate ester monomer(s) described above.

In one preferred aspect, the co-monomer(s) having an ethylenically unsaturated group include, but are not limited to, the group of polar monomers, in particular non-acid functional polar monomers.

In another aspect of the present disclosure, the co-monomer(s) having an ethylenically unsaturated group are selected from the group of non-acid functional polar monomers having a single ethylenically unsaturated group and a nitrogen-containing group or a salt thereof. In a typical aspect, the nitrogen-containing group is selected from secondary amido groups and tertiary amido groups, in particular those selected from the group consisting of N-vinyl lactams.

Advantageoulsy, the co-monomer(s) having an ethylenically unsaturated group may be selected from the group consisting of N-vinyl lactams, in particular N-vinyl caprolactam, N-vinyl piperidone, N-vinyl pyrrolidone; acryloyl morpholine, acrylamides and substituted acrylamides; in particular t-butyl acrylamide, dimethylamino ethyl acrylamide, N-octyl acrylamide, N,N-dialkyl acrylamides, N-methyl acrylamide, N-ethyl acrylamide, N-isopropyl acrylamide, tert-octyl acrylamide, N,N-dimethyl acrylamide, N,N-diethyl acrylamide, N,N-dipropyl acrylamide, N,N-dibutyl acrylamide; and any combinations or mixtures thereof. Preferably, the co-monomer(s) having an ethylenically unsaturated group comprise N-vinyl caprolactam. Preferably still, the co-monomer having an ethylenically unsaturated is selected to be N-vinyl caprolactam.

Without wishing to be bound by theory, it is believed that the co-monomer(s) having an ethylenically unsaturated group selected from the group of non-acid functional polar monomers having a single ethylenically unsaturated group and a nitrogen-containing group, and in particular those wherein the nitrogen-containing group is selected from the group consisting of N-vinyl lactams, do advantageously affect the curing mechanism. It is further believed that the co-monomer(s) having an ethylenically unsaturated group selected from the group of non-acid functional polar monomers having a single ethylenically unsaturated group and a nitrogen-containing group beneficially participate in the formation of an interpenetrating network involving the (meth)acrylate ester based (co)polymeric material and an aziridine network resulting from acid-catalyzed cationic ring-opening polymerization of polyfunctional aziridine monomeric units.

The co-monomer(s) having an ethylenically unsaturated group for use herein may be present in the (co)polymerizable material, in any suitable amounts. In some exemplary aspects, the co-monomer(s) having an ethylenically unsaturated group are present in amounts up to 40 parts by weight, up to 35 parts by weight, or even up to 30 parts by weight of the (co)polymerizable material. In some other exemplary aspects, this amount is typically of at least 5 parts by weight, or at least 10 parts by weight of the (co)polymerizable material.

Accordingly, in some exemplary aspects, the co-monomer(s) having an ethylenically unsaturated group are present in amounts in a range of from 0 to 40 parts, from 5 to 35 parts by weight, or even from 20 to 35 parts by weight of the (co)polymerizable material. In some other exelplary aspects, the co-monomer(s) having an ethylenically unsaturated group are present in amounts in a range of from 0 to 20 parts, from 5 to 15 parts by weight, or even from 5 to 10 parts by weight of the (co)polymerizable material.

In a particular aspect of the curable precursor of the present disclosure, the (co)polymerizable material comprises:
  a) from 60 to 100 parts by weight, from 65 to 95 parts by weight, or even from 65 to 80 parts by weight, of a (meth)acrylate ester monomer; and
  b) optionally, from 0 to 40 parts by weight, from 5 to 35 parts by weight, or even from 20 to 35 parts by weight, of a co-monomer having an ethylenically unsaturated group.

In some exemplary aspects, the (co)polymerizable material suitable for preparing the (co)polymeric material of the curable precursor, comprises a second co-monomer having an ethylenically unsaturated group. Suitable second co-monomer(s) having an ethylenically unsaturated group for use herein will be easily identified by those skilled in the art, in the light of the present description. As such, the second co-monomer(s) having an ethylenically unsaturated group for use herein are not particularly limited.

In one exemplary aspect, the second co-monomer(s) having an ethylenically unsaturated group include, but are not limited to, the group consisting of high Tg monomers. In the context of the present disclosure, the expression "high Tg monomer" is meant to refer to monomers having a Tg of at least 25° C., preferably at least 50° C. (wherein the Tg of a monomer is measured as a homopolymer prepared from the monomer).

Suitable high Tg monomers for use herein include, but are not limited to, those selected from the group consisting of t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, propyl methacrylate, and any combinations or mixtures thereof.

According to a particular aspect of the curable precursor according to the disclosure, the (co)polymerizable material comprises:
 a) from 50 to 100 parts by weight, from 60 to 90 parts by weight, or even from 65 to 80 parts by weight, of a (meth)acrylate ester monomer; and
 b) optionally, from 0 to 20 parts by weight, from 5 to 15 parts by weight, or even from 5 to 10 parts by weight, of a co-monomer having an ethylenically unsaturated group; and
 c) optionally, from 0 to 30 parts by weight, from 5 to 25 parts by weight, or even from 15 to 25 parts by weight, of a second co-monomer having an ethylenically unsaturated group.

According to a particular aspect of the curable precursor according to the disclosure, the (co)polymerizable material is free of acid functional monomers.

In order to increase cohesive strength of the pressure sensitive adhesive, a multifunctional (meth)acrylate may optionally be incorporated into the blend of polymerizable monomers. Examples of useful multifunctional (meth)acrylate include, but are not limited to, di(meth)acrylates, tri(meth)acrylates, and tetra(meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth)acrylate is tailored depending upon application of the adhesive composition. Typically, the multifunctional (meth)acrylate is present in amounts less than 5 parts based on total dry weight of adhesive composition. More specifically, the crosslinker may be present in amounts from 0.01 to 5 parts, preferably 0.05 to 1 parts, based on 100 parts total monomers (polymerized or unpolymerized) of the adhesive composition.

Generally, the (co)polymerizable material (pre-polymerization monomer mixture) used to prepare the (co)polymeric material, includes an appropriate initiator. For polymerization by ultraviolet light, a photoinitiator is included. Useful photoinitiators include substituted acetophenones such as benzyl dimethyl ketal and 1-hydroxycyclohexyl phenyl ketone, substituted alpha-ketols such as 2-methyl-2-hydroxypropiophenone, benzoin ethers such as benzoin methyl ether, benzoin isopropyl ether, substituted benzoin ethers such as anisoin methyl ether, aromatic sulfonyl chlorides, photoactive oximes and azo-type initiators. The photoinitiator may be used in an amount from about 0.001 to about 5.0 parts by weight, preferably from about 0.01 to about 5.0 parts by weight, more preferably in an amount from 0.05 to 0.5 parts by weight, and more preferably in an amount from 0.05 to 0.3 parts by weight per 100 parts by weight of total monomer.

The pre-polymerization monomer mixture used to prepare the acrylate the (co)polymeric material, may also be polymerized by thermal polymerization or by a combination of thermal and radiation polymerization. For thermal polymerization, a thermal initiator is included. Thermal initiators useful in the present invention include, but are not limited to azo, peroxide, persulfate, and redox initiators. Azo-type initiators, such as e.g. the "Vazo" line, commercially available from DuPont Chemical Co., are particularly preferred. The thermal initiator may be used in an amount from about 0.01 to about 5.0 parts by weight per 100 parts by weight of total monomer, preferably from 0.025 to 2 weight percent.

The (co)polymerizable material may optionally further comprise chain transfer agents to control the molecular weight of the resultant polymer. Examples of useful chain transfer agents include but are not limited to those selected from the group consisting of carbon tetrabromide, alcohols, mercaptans, and mixtures thereof. When present, the preferred chain transfer agents are isooctylthioglycolate and carbon tetrabromide. The emulsion mixture may further comprise up to about 0.5 parts by weight of a chain transfer agent, typically about 0.01 to about 0.5 parts by weight, if used, preferably about 0.05 parts by weight to about 0.2 parts by weight, based upon 100 parts by weight of the total monomer mixture.

The curable precursor according to the disclosure further comprises a polyfunctional aziridine curing agent. Suitable polyfunctional aziridine curing agents for use herein will be easily identified by those skilled in the art, in the light of the present description. As such, the polyfunctional aziridine curing agents for use herein are not particularly limited. Suitable polyfunctional aziridine curing agents for use herein are described e.g. in US-A1-2011/0178248 (Kavanagh et al.), the content of which is herewith incorporated by reference.

In one exemplary aspect, the polyfunctional aziridine curing agents comprise at least two aziridine functional groups, in particular two or three aziridine functional groups. In another exemplary aspect, the polyfunctional aziridine curing agents comprise at least one aziridine functional group and at least one (meth)acryloyl functional group.

According to a particular aspect of the present disclosure, the polyfunctional aziridine curing agent for use herein has the following formula:

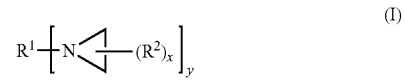
(I)

wherein
$R^1$ is a (hetero)hydrocarbyl group;
$R^2$ is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group; preferably $R^2$ is H, $CH_2$, $C_2H_5$ or even phenyl group;
x is 0, 1 or 2, and
y is at least 1, preferably 1 to 4, or even 2 to 3.

According to another particular aspect of the present disclosure, the polyfunctional aziridine curing agent for use herein has the following formula:

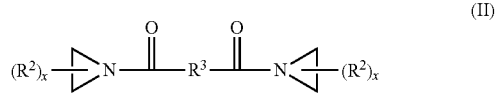
(II)

wherein
R³ is a (hetero)hydrocarbyl group;
R² is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group; preferably R² is H, $CH_2$, $C_2H_5$ or even phenyl group; and
x is 0, 1 or 2.

According to another particular aspect of the present disclosure, the polyfunctional aziridine curing agent for use herein has the following formula:

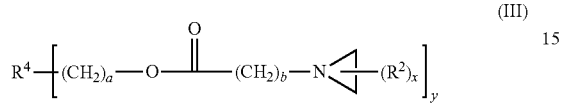
(III)

wherein
R⁴ is a (hetero)hydrocarbyl group having a valency of y;
R² is an H or $C_1$-$C_{12}$ alkyl group, $C_1$-$C_5$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group; preferably R² is H, $CH_2$, $C_2H_5$ or even phenyl group;
y is at least 1, preferably 1 to 4, or even 2 to 3;
x is 0, 1 or 2; and
each of a and b are independently 0 to 6, 0 to 4, or even 0 to 2.

According to still another particular aspect of the present disclosure, the polyfunctional aziridine curing agent for use herein has the following formula:

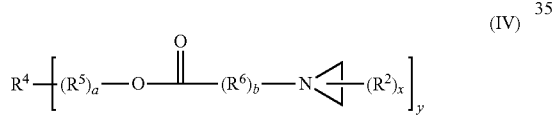
(IV)

wherein
R⁴ is a (hetero)hydrocarbyl group having a valency of y;
R⁵ and R⁶ are independently (hetero)hydrocarbyl groups;
R² is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group; preferably R² is H, $CH_2$, $C_2H_5$ or even phenyl group;
y is at least 1, preferably 1 to 4, or even 2 to 3;
x is 0, 1 or 2; and
each of a and b are independently 0 to 6, 0 to 4, or even 0 to 2.

According to still another particular aspect of the present disclosure, the polyfunctional aziridine curing agent for use herein has the following formula:

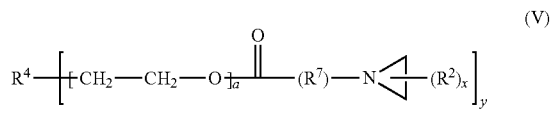
(V)

wherein
R⁴ is a (hetero)hydrocarbyl group having a valency of y;
R⁷ is a (hetero)hydrocarbyl group, in particular $C_2$-$C_{12}$ alkyl group, $C_2$-$C_8$ alkyl group, $C_2$-$C_6$ alkyl group, or even $CH_2$—CHR'—O-group, with R' being H or $CH_3$;
R² is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group; preferably R² is H, $CH_2$, $C_2H_5$ or even phenyl group;
y is at least 1, preferably 1 to 4, or even 2 to 3;
x is 0, 1 or 2; and
a is 0 to 100, 1 to 50, 1 to 20 or even 1 to 10.

According to still another particular aspect of the present disclosure, the polyfunctional aziridine curing agent for use herein has the following formula:

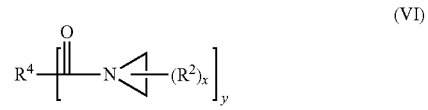
(VI)

wherein
R⁴ is a hydrocarbyl group having a valency of y;
R² is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group; preferably R² is H, $CH_2$, $C_2H_5$ or even phenyl group;
y is at least 1, preferably 1 to 4, or even 2 to 3; and
x is 0, 1 or 2.

According to still another particular aspect of the present disclosure, the polyfunctional aziridine curing agents for use herein have the following formula:

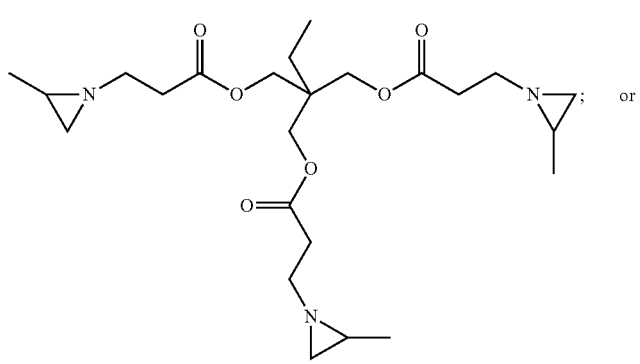
A)

or

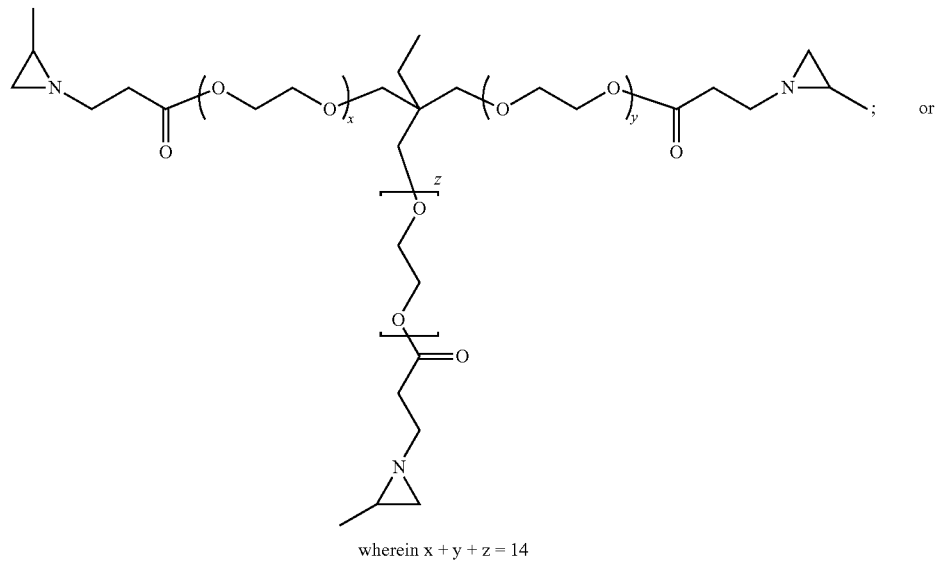

B)

wherein x + y + z = 14

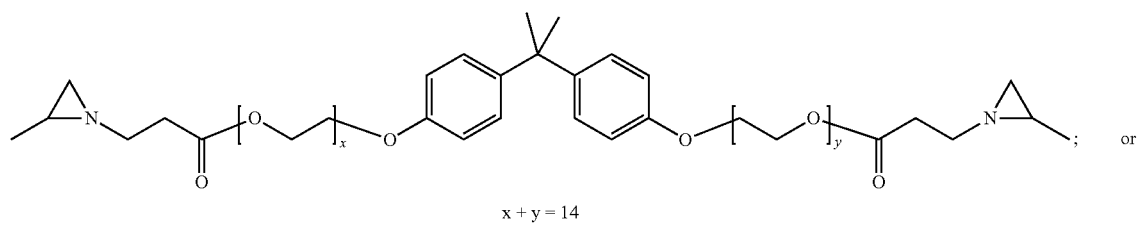

C)

x + y = 14

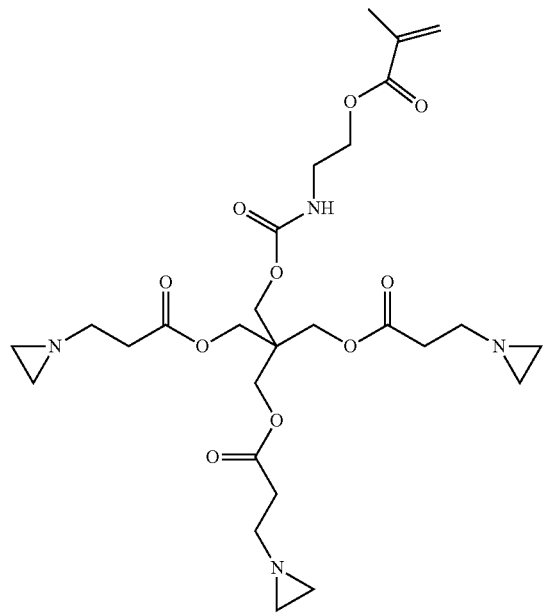

D)

The curable precursor according to the disclosure further comprises an acid generating agent. Suitable acid generating agents for use herein will be easily identified by those skilled in the art, in the light of the present description. As such, the acid generating agents for use herein are not particularly limited. Suitable acid generating agents for use herein are described e.g. in U.S. Pat. No. 5,089,536 (Palazzotto), US-A1-2011/0178248 (Kavanagh et al.) and U.S. Pat. No. 5,721,289 (Karim et al.) incorporated herein by reference.

In one typical aspect, the acid generating agents are selected from the group consisting of thermal acid generating agents, photo acid generating agents, and any combinations or mixtures thereof. As will be apparent to those skilled in the art, some acid generating agents may operate as both thermal- and photo acid generating agents.

Without wishing to be bound by theory, it is believed that the (super) acid generated by the acid generating agents initiates the ring-opening homopolymerization of the polyfunctional aziridine curing agents acting as monomeric units.

Suitable thermal acid generating agents are for example selected from the group consisting of quarternary blocked superacids, amine blocked superacids, and any combinations or mixtures thereof.

Exemplary quarternary blocked superacids for use herein are quarternary blocked $SbF_6$, quarternary blocked triflic acid, and any combinations thereof. Exemplary suitable thermal acid generating agents are for example commercially available from King Industries under tradename K-Pure CXC and TAG series.

In a particular aspect, the acid generating agents for use herein are selected from the group consisting of quarternary blocked $SbF_6$, quarternary blocked triflic acid, quarternary blocked fluorosulfonic acids, and any combinations or mixtures thereof.

Suitable photo acid generating agents are for example selected from the group consisting of ionic salts of organometallic complexes and onium salts, in particular sulfonium and iodonium salts. Exemplary organic onium salts for use herein are iodonium or sulfonium or phenyliodonium salts of the anions $SbF_6-$, $PF_6-$, $CF_3SO_3-$, $C_4F_9SO_3-$ and $C_8F_{17}SO_3-$, and any combinations or mixtures thereof. Exemplary suitable photo acid generating agents are for example commercially available from Bluestar Silicones under tradename Rhodorsil 2074, from Wako Chemicals under tradename WPI 113 (Iodonium salt), from Hampford Research Inc. under tradename FP 5386, or from BASF under tradenames CGI 1907 or Irgacure 290 (Sulfonium salt).

The curable precursor according to the disclosure, may in some aspects further comprise a filler material which is preferably selected from the group consisting of filler particles, in particular expanded perlite, microspheres, expendable microspheres, glassbeads, glass microspheres, silica type fillers, hydrophobic silica type fillers, hydrophilic silica type fillers, hydrophobic fumed silica, hydrophilic fumed silica, fibers, electrically and/or thermally conducting particles, nanoparticles, in particular silica nanoparticles, and any combinations or mixtures thereof. The disclosure is however not that limited as alternative filler material may be easily identified by those skilled in the art, in the light of the present disclosure. In a particular aspect, the filler material, in particular the particulate filler material comprises hollow glass microspheres.

The filler material for use herein may be present in the curable precursor of a pressure sensitive adhesive, in any suitable amounts. In some exemplary aspects, the filler material is present in amounts up to 30 parts by weight, up to 25 parts by weight, or even up to 20 parts by weight of the curable precursor of a pressure sensitive adhesive. In some other exemplary aspects, this amount is typically of at least 1 part by weight, or at least 3 parts by weight of the curable precursor of a pressure sensitive adhesive.

Accordingly, in some exemplary aspects, the filler material is present in amounts in a range of from 1 to 20 parts, from 3 to 15 parts by weight, or even from 5 to 13 parts by weight of the curable precursor of a pressure sensitive adhesive.

In the context of this disclosure, the (co)polymeric material comprising the reaction product of a (co)polymerizable material comprising a (meth)acrylate ester monomer is present in the curable precursor of a pressure sensitive adhesive in an amount of 100 parts by weight to calculate the amounts of the remaining ingredients.

In a particular aspect, the curable precursor of the disclosure comprises:
a) 100 parts by weight of a (co)polymeric material comprising the reaction product of a (co)polymerizable material comprising a (meth)acrylate ester monomer; and optionally, a co-monomer having an ethylenically unsaturated group;
b) from 0.1 to 30 parts by weight, from 0.5 to 25 parts by weight, from 1 to 20 parts by weight, from 1 to 15 parts by weight, or even from 5 to 15 parts by weight, of a polyfunctional aziridine curing agent;
c) from 0.01 to 10 parts by weight, from 0.1 to 8 parts by weight, from 0.2 to 6 parts by weight, or even from 0.2 to 5 parts by weight, of an acid generating agent; and
d) optionally, from 1 to 20 parts by weight, from 3 to 15 parts by weight, or even from 5 to 13 parts by weight, of a filler material, preferably hollow glass microspheres.

The curable precursor of a pressure sensitive adhesive may also contain one or more conventional additives. Preferred additives include tackifiers, plasticizers, dyes, antioxidants, and UV stabilizers. Such additives can be used if they do not affect the superior properties of the pressure sensitive adhesives.

If tackifiers are used, then up to about 50% by weight, preferably less than 30% by weight, and more preferably less than 5% by weight based on the dry weight of the total adhesive polymer would be suitable. The type and amount of tackifier can affect properties such as contactability, bonding range, bond strength, heat resistance and specific adhesion.

Suitable tackifying resins include, for example, terpene phenolics, rosins, rosin esters, esters of hydrogenated rosins, synthetic hydrocarbon resins and combinations thereof. Especially suitable tackifying resins include the commercially available tackifying resins: FORAL 85E (a glycerol ester of highly hydrogenated refined gum rosin) commercially available from Eastman, Middelburg, NL), FORAL 3085 (a glycerol ester of highly hydrogenated refined wood rosin) commercially available from Hercules Inc., Wilmington, Del.; ESCOREZ 2520 and ESCOREZ 5615 (aliphatic/aromatic hydrocarbon resins) commercially available from ExxonMobil Corp., Houston, Tex.; and Regalite 7100 (a partially hydrogenated hydrocarbon resin) commercially available from Eastman, Kingsport, Tenn.

The curable precursor of a pressure sensitive adhesive may contain a plasticizer, if desired. The plasticizer is typically selected to be compatible with (i.e., miscible with) the other components in the composition such as the polymerizable material and any optional tackifier. Suitable plasticizers include, but are not limited to, various polyalkylene oxides (e.g., polyethylene oxides or propylene oxides), adipic acid esters, formic acid esters, phosphoric acid esters, benzoic acid esters, phthalic acid esters, and sulfonamides, or naphthenic oils.

The (co)polymeric material may be prepared by any conventional free radical polymerization method, including solution, radiation, bulk, dispersion, emulsion, solventless, and suspension processes. Generally, the pre-polymerization monomer mixture used to prepare the (co)polymeric material, includes an appropriate initiator.

As will be apparent to those skilled in the art, the curable precursor of a pressure sensitive adhesive according to the present disclosure may further include a variety of additional additives depending on the envisaged properties for the resulting cured pressure sensitive adhesive. Exemplary additional additives include, but are not limited to, one or more plasticizers, UV stabilizers, antistatic agents, colorants, antioxidants, fungicides, bactericides, organic and/or inorganic filler particles, pigments, and any combinations thereof. Advantageously, the additional additives for use herein are non-polymerizable additives. As will be apparent to those skilled in the art, additional additives for use herein may be included at appropriate timing and in the appropriate polymeric or pre-polymeric matrix.

One exemplary method of preparing a curable precursor of a pressure sensitive adhesive comprises partially polymerizing monomers to produce a syrup polymer comprising the (meth)acrylate copolymer and unpolymerized monomers. Generally, the polyfunctional aziridine curing agent, the acid generating agent, and optionally the co-monomer having an ethylenically unsaturated group, are added to the partially polymerized composition, then coated on a suitable substrate and further polymerized. The syrup polymer composition is polymerized to a useful coating viscosity, which may be coated onto a substrate (such as a tape backing) and further polymerized. Partial polymerization provides a coatable solution of the (meth)acrylate copolymer.

In an alternative exemplary method of preparing a curable precursor of pressure sensitive adhesive, the (meth)acrylate copolymer is prepared by solution methods. A typical solution polymerization method is carried out by adding the monomers, a suitable solvent, and an optional chain transfer agent to a reaction vessel, adding a free radical initiator, purging with nitrogen, and maintaining the reaction vessel at an elevated temperature, typically in the range of about 40 to 100° C. until the reaction is completed, typically in about 1 to 20 hours, depending upon the batch size and temperature. Examples of the solvent are methanol, tetrahydrofuran, ethanol, isopropanol, acetone, methyl ethyl ketone, methyl acetate, ethyl acetate, toluene, xylene, and an ethylene glycol alkyl ether. These solvents can be used alone or as mixtures thereof. Generally, the polyfunctional aziridine curing agent and the acid generating agent are added to a solution of the (meth)acrylate copolymer thereby forming a coating solution, then coated on a suitable substrate and further dried in an oven.

The polymerizations may be conducted in the presence of, or preferably in the absence of, suitable solvents such as ethyl acetate, toluene and tetrahydrofuran which are unreactive with the functional groups of the components of the syrup polymer.

Polymerization can be accomplished by exposing the syrup polymer composition to energy in the presence of a photoinitiator. Energy activated initiators may be unnecessary where, for example, ionizing radiation is used to initiate polymerization.

A preferred method of preparation of the coatable syrup polymer is photoinitiated free radical polymerization. Advantages of the photopolymerization method are that 1) heating the monomer solution is unnecessary and 2) photoinitiation is stopped completely when the activating light source is turned off.

Polymerization to achieve a coatable viscosity may be conducted such that the conversion of monomers to polymer is up to about 30%. Polymerization can be terminated when the desired conversion and viscosity have been achieved by removing the light source and by bubbling air (oxygen) into the solution to quench propagating free radicals. The solute polymer(s) may be prepared conventionally in a non-monomeric solvent and advanced to high conversion (degree of polymerization). When solvent (monomeric or non-monomeric) is used, the solvent may be removed (for example by vacuum distillation) either before or after formation of the syrup polymer. While an acceptable method, this procedure involving a highly converted functional polymer is not preferred because an additional solvent removal step is required, another material may be required (the non-monomeric solvent), and dissolution of the high molecular weight, highly converted solute polymer in the monomer mixture may require a significant period of time.

Useful photoinitiators include benzoin ethers such as benzoin methyl ether and benzoin isopropyl ether; substituted acetophenones such as 2,2-dimethoxyacetophenone, available as Irgacure™ 651 photoinitiator (Ciba-Geigy Corp.; Ardsley, N.Y.), 2,2 dimethoxy-2-phenyl-1-phenylethanone, available as Esacure™ KB-1 photoinitiator (Sartomer Co.; West Chester, Pa.), and dimethoxyhydroxyacetophenone; substituted α-ketols such as 2-methyl-2-hydroxy propiophenone; aromatic sulfonyl chlorides such as 2-naphthalene-sulfonyl chloride; and photoactive oximes such as 1-phenyl-1,2-propanedione-2-(O-ethoxy-carbonyl)oxime. Particularly preferred among these are the substituted acetophenones.

Preferred photoinitiators are photoactive compounds that undergo a Norrish I cleavage to generate free radicals that can initiate by addition to the acrylic double bonds. The photoinitiator can be added to the mixture to be coated after the copolymer has been formed, i.e., photoinitiator can be added to the syrup polymer mixture. Such polymerizable photoinitiators are described, for example, in U.S. Pat. No. 5,902,836 (Bennett et al.) and U.S. Pat. No. 5,506,279 (Babu et al.).

The syrup polymer composition and the photoinitiator may be irradiated with activating UV radiation to polymerize the monomer component(s). UV light sources can be of two types: 1) relatively low light intensity sources such as Blacklights which provide generally 10 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities generally greater than 10 mW/cm$^2$, preferably between 15 and 450 mW/cm$^2$. Where actinic radiation is used to fully or partially polymerize the syrup polymer composition, high intensities and short exposure times are preferred. For example, an intensity of 600 mW/cm$^2$ and an exposure time of about 1 second may be used successfully. Intensities can range from about 0.1 to about 150 mW/cm$^2$, preferably from about 0.5 to about 100 mW/cm$^2$, and more preferably from about 0.5 to about 50 mW/cm$^2$. Such photoinitiators preferably are present in an amount of from 0.1 to 1.0 pbw per 100 pbw of the syrup polymer composition.

Accordingly, relatively thick coatings (e.g., at least about 1 mil or 25.4 micrometers) can be achieved when the extinction coefficient of the photoinitiator is low.

The degree of conversion can be monitored during the irradiation by measuring the index of refraction of the polymerizing medium as previously described. Useful coating viscosities are achieved with conversions (i.e. the percentage of available monomer polymerized) in the range of up to 30%, preferably 2-20%, more preferably from 5-15%, and most preferably from 7-12%. The molecular weight (weight average) of the solute polymer(s) is at least 100,000, preferably at least 500,000.

When preparing pressure sensitive adhesives, it is expedient for the photoinitiated polymerization reactions to proceed to virtual completion, i.e., depletion of the monomeric components, at temperatures less than about 70° C. (preferably at 50° C. or less) with reaction times less than 24 hours, preferably less than 12 hours, and more preferably less than 6 hours. These temperature ranges and reaction rates obviate the need for free radical polymerization inhibitors, which are often added to acrylic systems to stabilize against undesired, premature polymerization and gelation. Furthermore, the addition of inhibitors adds extraneous material that will remain with the system and inhibit the desired polymerization of the syrup polymer and formation of the cured pressure sensitive adhesives of the disclosure. Free radical polymerization inhibitors are often required at processing temperatures of 70° C. and higher for reaction periods of more than about 6 to 10 hours.

It is preferable to coat the curable precursor of pressure sensitive adhesive soon after preparation. The curable precursor composition of pressure sensitive adhesive, either as a syrup or solution are easily coated upon suitable substrates, such as flexible backing materials, by conventional coating techniques, then further polymerized, and cured or dried, to produce adhesive coated sheet materials. The flexible backing material may be any material conventionally utilized as a tape backing, optical film or any other flexible material.

Adhesive articles may be prepared by coating the curable precursor composition of a pressure sensitive adhesive on a suitable support, such as a flexible backing. Examples of materials that can be included in the flexible backing include polyolefins such as polyethylene, polypropylene (including isotactic polypropylene), polystyrene, polyester, polyvinyl alcohol, poly(ethylene terephthalate), poly(butylene terephthalate), poly(caprolactam), poly(vinylidene fluoride), polylactides, cellulose acetate, and ethyl cellulose and the like. Commercially available backing materials useful in the invention include kraft paper (available from Monadnock Paper, Inc.); cellophane (available from Flexel Corp.); spunbond poly(ethylene) and poly(propylene), such as Tyvek™ and Typar™ (available from DuPont, Inc.); and porous films obtained from poly(ethylene) and poly(propylene), such as Teslin™ (available from PPG Industries, Inc.), and Cellguard™ (available from Hoechst-Celanese).

Backings may also be prepared of fabric such as woven fabric formed of threads of synthetic or natural materials such as cotton, nylon, rayon, glass, ceramic materials, and the like or nonwoven fabric such as air laid webs of natural or synthetic fibers or blends of these. The backing may also be formed of metal, metalized polymer films, or ceramic sheet materials may take the form of any article conventionally known to be utilized with pressure sensitive adhesive compositions such as labels, tapes, signs, covers, marking indicia, and the like.

The above-described precursor compositions are coated on a substrate using conventional coating techniques modified as appropriate to the particular substrate. For example, these compositions can be applied to a variety of solid substrates by methods such as roller coating, flow coating, dip coating, spin coating, spray coating, knife coating, and die coating. These various methods of coating allow the compositions to be placed on the substrate at variable thicknesses thus allowing a wider range of use of the compositions. Coating thicknesses may vary as previously described.

The syrup polymers may be of any desirable concentration for subsequent coating, but is typically between 2 to 20 wt. % polymer solids in monomer, preferably 5 to 15 wt. %. The desired concentration may be achieved by further dilution of the coating composition, or by partial drying.

The flexible support may also comprise a release-coated substrate. Such substrates are typically employed when an adhesive transfer tape is provided. Examples of release-coated substrates are well known in the art and include, by way of example, silicone-coated kraft paper and the like. Tapes of the invention may also incorporate a low adhesion backing (LAB), which are known in the art.

According to another aspect, the present disclosure relates to a cured pressure sensitive adhesive obtainable by curing the curable precursor as above-described. In this context, the curing step is preferably performed by allowing acid to be released into the curable precursor of a pressure sensitive adhesive.

In a preferred aspect of the cured pressure sensitive adhesive according to the disclosure, the curing step is performed by subjecting the curable precursor of a pressure sensitive adhesive to a triggering energy sufficient to allow the acid generating agent to release acid into the curable precursor of a pressure sensitive adhesive, and wherein the triggering energy is preferably selected from the group of thermal energy or actinic radiation, more preferably UV radiation.

In still another aspect of the present disclosure, it is provided a composite assembly comprising a substrate and a curable precursor of a pressure sensitive adhesive, as above-described, applied onto at least part of the surface of the substrate, thereby forming a layer of a curable precursor of a pressure sensitive adhesive.

According to an alternative execution of the composite assembly, the layer of a curable precursor of a pressure sensitive adhesive is cured, preferably by allowing acid to be released into the curable precursor of a pressure sensitive adhesive.

In a preferred aspect of the composite assembly according to the disclosure, the curing step is performed by subjecting the curable precursor of a pressure sensitive adhesive to a triggering energy sufficient to allow the acid generating agent to release acid into the curable precursor of a pressure sensitive adhesive, and wherein the triggering energy is preferably selected from the group of thermal energy or actinic radiation, more preferably UV radiation.

Advantageoulsy, the composite assembly according to the present disclosure is an adhesive article, wherein the substrate is preferably a flexible backing layer.

According to an advantageous aspect of the composite assembly, the layer of a curable precursor of a pressure sensitive adhesive takes the form of a polymeric foam layer. According to this beneficial aspect, properties/requirements of the overall composite assembly such as application issues, deforming issues and energy distribution may be advantageously addressed by appropriate formulation of this polymeric foam layer, while other properties such as adhesion (quick adhesion) can be adjusted by the formulation of other non-foam pressure sensitive adhesive layers (also commonly referred to as skin layers).

In the context of the present disclosure, the term "polymeric foam" is meant to designate a material based on a polymer and which material comprises voids, typically in an amount of at least 5% by volume, typically from 10% to 55% by volume or from 10% to 45% by volume. The voids may be obtained by any of the known methods such as cells formed by gas. Alternatively, the voids may result from the incorporation of hollow fillers, such as hollow polymeric particles, hollow glass microspheres or hollow ceramic microspheres.

A polymeric foam layer for use herein has for example a thickness comprised between 100 and 6000 µm, between 200 and 4000 µm, between 500 and 2000 µm, or even between 800 and 1500 µm. As will be apparent to those skilled in the art, in the light of the present description, the preferred thickness of the polymeric foam layer will be dependent on the intended application.

A polymeric foam layer typically has a density comprised between 0.45 g/cm$^3$ and 1.5 g/cm$^3$, between 0.45 g/cm$^3$ and 1.10 g/cm$^3$, between 0.50 g/cm$^3$ and 0.95 g/cm$^3$, between 0.60 g/cm$^3$ and 0.95 g/cm$^3$, or even between 0.70 g/cm$^3$ and 0.95 g/cm$^3$. This density is achieved by including voids or cells. Typically, the polymeric foam layer will comprise at least 5% of voids by volume and for example between 15 and 45%, or between 20% and 45% by volume.

The voids or cells in the polymeric foam layer can be created in any of the known manners described in the art and include the use of a gas or blowing agent and/or including hollow particles into the composition for the polymeric foam layer. For example, according to one method to create a polymeric foam described in U.S. Pat. No. 4,415,615, an acrylic foam can be obtained by the steps of (i) frothing a composition containing the acrylate monomers and optional comonomers, (ii) coating the froth on a backing and (iii) polymerizing the frothed composition. It is also possible to coat the unfrothed composition of the acrylate monomers and optional comonomers to the backing and to then simultaneously foam and polymerize that composition. Frothing of the composition may be accomplished by whipping a gas into the polymerizable composition. Preferred gasses for this purpose are inert gasses such as nitrogen and carbon dioxide, particularly if the polymerization is photoinitiated.

According to still another aspect, it is provided a (post) curing system for pressure sensitive adhesives, comprising a polyfunctional aziridine curing agent and an acid generating agent.

According to yet another aspect, the present disclosure is directed to a method of applying a pressure sensitive adhesive to a substrate, comprising the steps of:
a) providing a curable precursor of a pressure sensitive adhesive comprising:
 i. a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
 ii. a polyfunctional aziridine curing agent; and
 iii. optionally, an acid generating agent;
b) applying the curable precursor of a pressure sensitive adhesive to at least part of the surface of the substrate; and
c) curing the curable precursor of a pressure sensitive adhesive by allowing acid to be released into it.

According to another aspect, the present disclosure is directed to a method of applying a pressure sensitive adhesive to a substrate, comprising the steps of:
a) providing a curable precursor of a pressure sensitive adhesive comprising:
 i. a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
 ii. a polyfunctional aziridine curing agent; and
 iii. optionally, an acid generating agent;
b) partially curing the curable precursor of a pressure sensitive adhesive by allowing acid to be released into it;
c) applying the partially cured pressure sensitive adhesive to at least part of the surface of the substrate; and
d) allowing the partially cured pressure sensitive adhesive to fully cure onto the substrate.

In a preferred aspect of the methods of applying a pressure sensitive adhesive to a substrate, as described above, the curing step is performed by subjecting the curable precursor of a pressure sensitive adhesive to a triggering energy sufficient to allow the acid generating agent to release acid into the curable precursor of a pressure sensitive adhesive, and wherein the triggering energy is preferably selected from the group of thermal energy or actinic radiation, more preferably UV radiation.

In an alternative execution of the methods of applying a pressure sensitive adhesive to a substrate, as described above, the curing step is performed by contacting the curable precursor of a pressure sensitive adhesive with a source of acid.

Suitable source of acids for use herein may be easily identified by those skilled in the art, in the light of the present disclosure. Suitable examples of sources of acid are for example selected from the group consisting of acid-containing compositions, acid-containing layers, acid-containing priming compositions, and any combinations or mixtures thereof.

In yet another aspect of the present disclosure, it is provided a method of preparing a cured pressure sensitive adhesive, comprising the steps of:
a) providing a curable precursor of a pressure sensitive adhesive comprising:
 i. a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
 ii. a polyfunctional aziridine curing agent; and
 iii. optionally, an acid generating agent; and
b) curing the curable precursor of a pressure sensitive adhesive by allowing acid to be released into it.

In a preferred aspect of the method of preparing a cured pressure sensitive adhesive, as described above, the curing step is performed by subjecting the curable precursor of a pressure sensitive adhesive to a triggering energy sufficient to allow the acid generating agent to release acid into the curable precursor of a pressure sensitive adhesive, and wherein the triggering energy is preferably selected from the group of thermal energy or actinic radiation, more preferably UV radiation.

In an alternative execution of the method of preparing a cured pressure sensitive adhesive, as described above, the curing step is performed by contacting the curable precursor of a pressure sensitive adhesive with a source of acid.

Suitable source of acids for use herein may be easily identified by those skilled in the art, in the light of the present disclosure. Suitable examples of sources of acid are for example selected from the group consisting of acid-containing compositions, acid-containing layers, acid-containing priming compositions, and any combinations or mixtures thereof.

In the context of the present disclosure, the curable precursor of a pressure sensitive adhesives, the (co)polymeric material comprising the reaction product of a (co)polymerizable material comprising a (meth)acrylic acid ester monomer, the (meth)acrylic acid ester monomers, the optional co-monomers having an ethylenically unsaturated group, the polyfunctional aziridine curing agents, and the optional acid generating agents for use in the methods as described above are identical to those described above with respect to the curable precursor of a pressure sensitive adhesive according to another aspect of the present disclosure.

In still another aspect, the present invention relates to the use of a combination of a polyfunctional aziridine curing agent and an acid generating agent for preparing a cured pressure sensitive adhesive comprising:
a) a (co)polymeric material comprising the reaction product of a (co)polymerizable material comprising a (meth)acrylate ester monomer; and
b) optionally, a co-monomer having an ethylenically unsaturated group and which is different from the (meth)acrylate ester monomer.

In yet another aspect, the present invention relates to the use of a curable precursor of a pressure sensitive adhesive or a cured pressure sensitive adhesive as above described, for the bonding to an uneven or irregular substrate.

In another particular aspect, the present invention relates to the use of a curable precursor of a pressure sensitive adhesive or a cured pressure sensitive adhesive as above described, for the bonding to a low surface energy substrate.

In yet another aspect, the present invention relates to the use of a curable precursor of a pressure sensitive adhesive or a cured pressure sensitive adhesive as above described, for industrial applications, in particular for construction applications and automotive applications. According to a particular aspect, the curable precursor of a pressure sensitive adhesive or the cured pressure sensitive adhesive as above described is used for automotive applications, in particular for taped seal on body applications for the automotive industry.

The curable precursor of a pressure sensitive adhesive or a cured pressure sensitive adhesive of the present disclosure may be used in any article conventionally known to use such assemblies such as labels, tapes, signs, covers, marking indices, display components, touch panels, and the like. Flexible backing materials having microreplicated surfaces are also contemplated.

The pressure sensitive adhesive assembly according to the present disclosure may be particularly useful for forming strong adhesive bonds to low surface energy (LSE) substrates. Included among such materials are polypropylene, polyethylene (e.g., high density polyethylene or HDPE), blends of polypropylene (e.g. PP/EPDM, TPO). Other substrates may also have properties of low surface energy due to a residue, such as an oil residue or a film, such as paint, being on the surface of the substrate.

The substrate to which the curable precursor of a pressure sensitive adhesive or a cured pressure sensitive adhesive may be applied is selected depending on the particular application. For example, the curable precursor of a pressure sensitive adhesive or a cured pressure sensitive adhesive may be applied to sheeting products (e.g., decorative graphics and reflective products), label stock, and tape backings. Additionally, the curable precursor of a pressure sensitive adhesive or a cured pressure sensitive adhesive may be applied directly onto other substrates such as a metal panel (e.g., automotive panel) or a glass window so that yet another substrate or object can be attached to the panel or window. Accordingly, the curable precursor of a pressure sensitive adhesive or a cured pressure sensitive adhesive of the present disclosure may find a particular use in the automotive manufacturing industry (e.g. for attachment of exterior trim parts or for weatherstrips), in the construction industry or in the solar panel construction industry.

Item 1 is a curable precursor of a pressure sensitive adhesive comprising:
a) a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
b) a polyfunctional aziridine curing agent; and
c) an acid generating agent.

Item 2 is the curable precursor according to item 1, wherein the polyfunctional aziridine curing agent comprises at least two aziridine functional groups, in particular two or three aziridine functional groups.

Item 3 is a curable precursor according to item 1, wherein the polyfunctional aziridine curing agent comprises at least one aziridine functional group and at least one (meth) acryloyl functional group.

Item 4 is a curable precursor according to any of the preceding items, wherein the polyfunctional aziridine curing agent has the following formula:

wherein
$R^1$ is a (hetero)hydrocarbyl group,
$R^2$ is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group;
preferably $R^2$ is H, $CH_2$, $C_2H_5$ or even phenyl group;
x is 0, 1 or 2, and
y is at least 1, preferably 1 to 4, or even 2 to 3.

Item 5 is a curable precursor according to any of the preceding items, wherein the polyfunctional aziridine curing agent has the following formula:

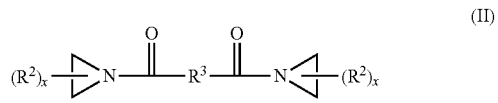

wherein
$R^3$ is a (hetero)hydrocarbyl group;
$R^2$ is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group;
preferably $R^2$ is H, $CH_2$, $C_2H_5$ or even phenyl group; and
x is 0, 1 or 2.

Item 6 is a curable precursor according to any of the preceding items, wherein the polyfunctional aziridine curing agent has the following formula:

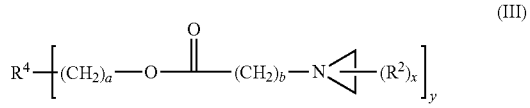

wherein
R⁴ is a (hetero)hydrocarbyl group having a valency of y;
R² is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group;
preferably R² is H, $CH_2$, $C_2H_5$ or even phenyl group;
y is at least 1, preferably 1 to 4, or even 2 to 3;
x is 0, 1 or 2; and
each of a and b are independently 0 to 6, 0 to 4, or even 0 to 2.

Item 7 is a curable precursor according to any of the preceding items, wherein the polyfunctional aziridine curing agent has the following formula:

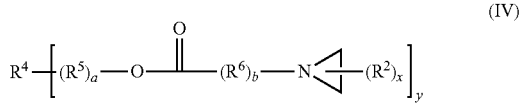

(IV)

wherein
R⁴ is a (hetero)hydrocarbyl group having a valency of y;
R⁵ and R⁶ are independently (hetero)hydrocarbyl groups;
R² is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group;
preferably R² is H, $CH_2$, $C_2H_5$ or even phenyl group;
y is at least 1, preferably 1 to 4, or even 2 to 3;
x is 0, 1 or 2; and
each of a and b are independently 0 to 6, 0 to 4, or even 0 to 2.

Item 8 is a curable precursor according to any of the preceding items, wherein the polyfunctional aziridine curing agent has the following formula:

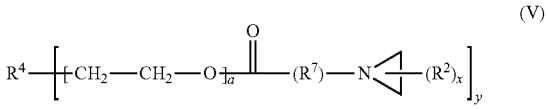

(V)

wherein
R⁴ is a (hetero)hydrocarbyl group having a valency of y;
R⁷ is a (hetero)hydrocarbyl group, in particular $C_2$-$C_{12}$ alkyl group, $C_2$-$C_8$ alkyl group, $C_2$-$C_6$ alkyl group, or even $CH_2$—CHR'—O-group, with R' being H or $CH_3$;
R² is an H or $C_1$-$C_{12}$ alkyl group, $C_1$-$C_8$ alkyl group, $C_1$-$C_6$ alkyl group, $C_1$-$C_4$ alkyl group, $C_1$-$C_2$ alkyl group, $C_6$-$C_{12}$ aromatic group, $C_6$-$C_{10}$ aromatic group, or even $C_6$-$C_7$ aromatic group;
preferably R² is H, $CH_2$, $C_2H_5$ or even phenyl group;
y is at least 1, preferably 1 to 4, or even 2 to 3;
x is 0, 1 or 2; and
a is 0 to 100, 1 to 50, 1 to 20 or even 1 to 10.

Item 9 is a curable precursor according to any of the preceding items, wherein the polyfunctional aziridine curing agent has any the following formula:

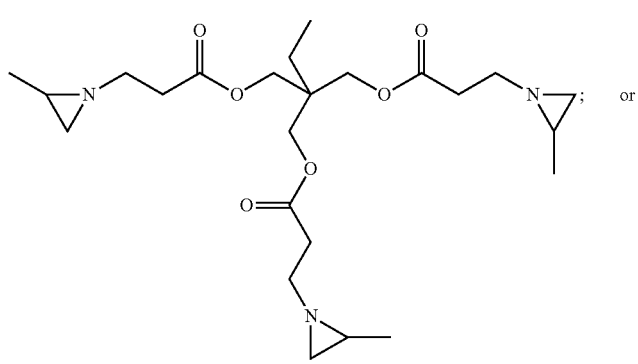

A)

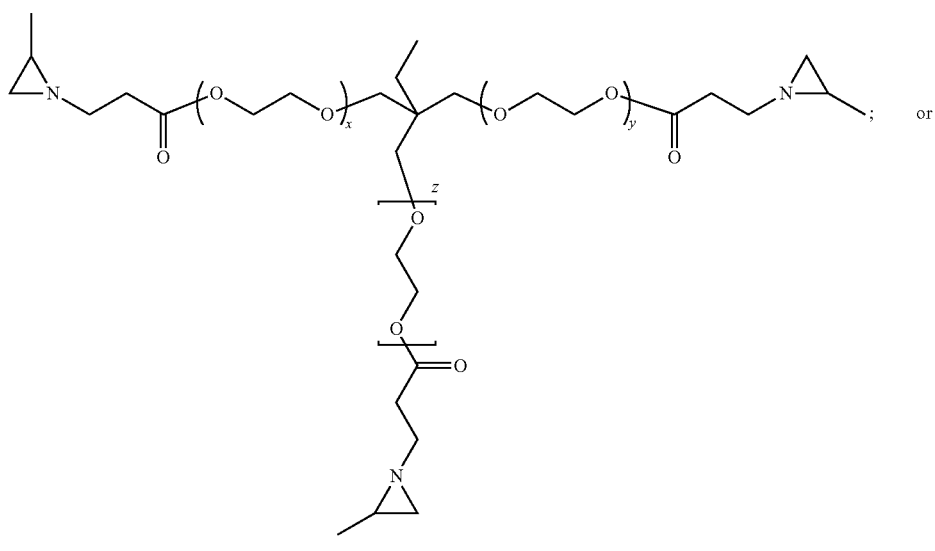

B)

wherein x + y + z = 14

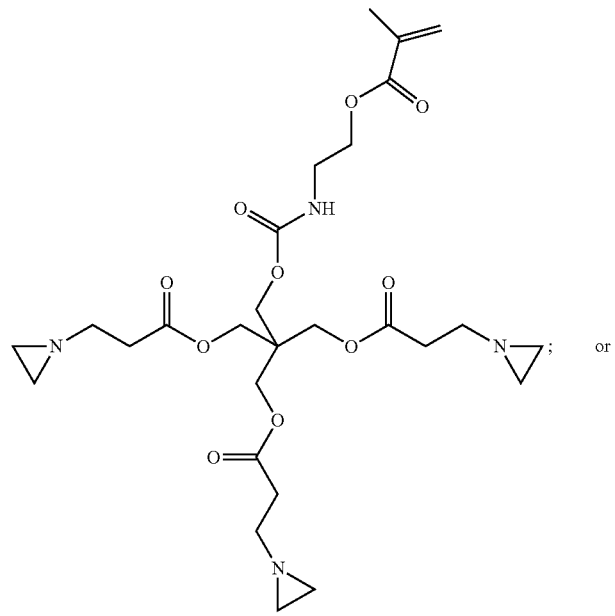
D)

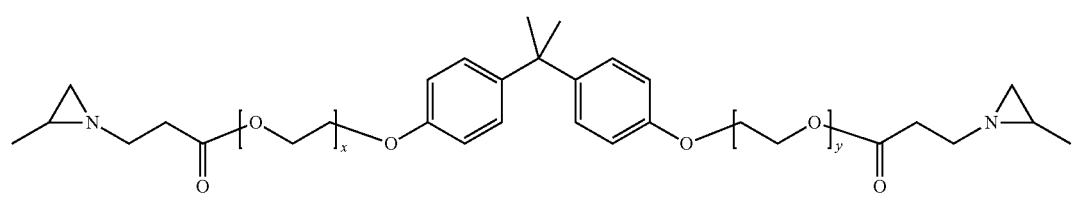
C)

x + y = 14

Item 10 is a curable precursor according to any of the preceding items, wherein the acid generating agent is selected from the group consisting of thermal acid generating agents, photo acid generating agents, and any combinations or mixtures thereof.

Item 11 is a curable precursor according to any of the preceding items, wherein the acid generating agent is a thermal acid generating agent selected from the group consisting of quarternary blocked superacids, amine blocked superacids, and any combinations or mixtures thereof.

Item 12 is a curable precursor according to any of the preceding items, wherein the acid generating agent is a thermal acid generating agent selected from the group consisting of quarternary blocked $SbF_6$, quarternary blocked triflic acid, quarternary blocked fluorosulfonic acids, and any combinations or mixtures thereof.

Item 13 is a curable precursor according to any of items 1 to 11, wherein the acid generating agent is a photo acid generating agent selected from the group consisting of ionic salts of organometallic complexes and onium salts, in particular iodonium or sulfonium salts, and any combinations or mixtures thereof.

Item 14 is a curable precursor according to item 13, wherein the acid generating agent is a photo acid generating agent selected from the group consisting of iodonium or sulfonium or phenyliodonium salts of the anions $SbF_6—$, $PF_6—$, $CF_3SO_3—$, $C_4F_9SO_3—$ and $C_8F_{17}SO_3—$, and any combinations or mixtures thereof.

Item 15 is a curable precursor according to any of the preceding items, wherein the (co)polymeric material comprises a polymer base material selected from the group consisting of polyacrylates whose main monomer component comprises a linear or branched alkyl (meth)acrylate ester, preferably a non-polar linear or branched alkyl (meth)acrylate ester having a linear or branched alkyl group comprising preferably from 1 to 32, from 1 to 20, or even from 1 to 15 carbon atoms.

Item 16 is a curable precursor according to any of the preceding items, wherein the (co)polymeric material comprises a polymer base material selected from the group consisting of polyacrylates whose main monomer component comprises a linear or branched alkyl (meth)acrylate ester selected from the group consisting of methyl (meth)acrylate, ethyl (meth)acrylate, n-propyl (meth)acrylate, iso-propyl (meth)acrylate, n-butyl acrylate, isobutyl acrylate, tert-butyl (meth)acrylate, n-pentyl (meth)acrylate, iso-pentyl (meth)acrylate, n-hexyl (meth)acrylate, iso-hexyl (meth)acrylate, cyclohexyl (meth)acrylate, phenyl (meth)acrylate, octyl (meth)acrylate, iso-octyl (meth)acrylate, 2-octyl(meth)acrylate, 2-ethylhexyl (meth)acrylate, decyl (meth)acrylate, lauryl (meth)acrylate, 2-propylheptyl (meth)acrylate, stearyl (meth)acrylate, isobornyl acrylate, benzyl (meth)acrylate, octadecyl acrylate, nonyl acrylate, dodecyl acrylate, isophoryl (meth)acrylate, and any combinations or mixtures thereof.

Item 17 is a curable precursor according to item 16, wherein the linear or branched alkyl (meth)acrylate ester is selected from the group consisting of iso-octyl (meth)acrylate, 2-ethylhexyl (meth)acrylate, 2-propylheptyl (meth)acrylate, 2-octyl (meth)acrylate, butyl acrylate, and any combinations or mixtures thereof, more preferably from the group consisting of iso-octyl acrylate, 2-ethylhexyl acrylate, 2-octyl acrylate, and 2-propylheptyl acrylate.

Item 18 is a curable precursor according to item 16 or 17, wherein the linear or branched alkyl (meth)acrylate ester comprises 2-ethylhexyl acrylate.

Item 19 is a curable precursor according to item 16 or 17, wherein the linear or branched alkyl (meth)acrylate ester comprises 2-octyl(meth)acrylate.

Item 20 is a curable precursor according to item 19, wherein at least 25 wt %, at least 50 wt %, at least 75 wt %, or even 100 wt % of the chemical structure of the 2-octyl (meth)acrylate is at least partly, preferably completely (i.e. 100 wt %) derived from biological material, more preferably from a plant material.

Item 21 is curable precursor according to any of the preceding items, wherein the optional co-monomer having an ethylenically unsaturated group is selected from the group of non-acid functional polar monomers.

Item 22 is a curable precursor according to any of the preceding items, wherein the optional co-monomer having an ethylenically unsaturated group is selected from the group of non-acid functional polar monomers having a single ethylenically unsaturated group and a nitrogen-containing group or a salt thereof.

Item 23 is a curable precursor according to item 22, wherein the nitrogen-containing group is selected from secondary amido groups and tertiary amido groups, in particular those selected from the group consisting of N-vinyl lactams.

Item 24 is a curable precursor according to item 22 or 23, wherein the optional co-monomer having an ethylenically unsaturated group is selected from the group consisting of N-vinyl caprolactam; N-vinyl piperidone, N-vinyl pyrrolidone; acryloyl morpholine, acrylamides and substituted acrylamides; in particular t-butyl acrylamide, dimethylamino ethyl acrylamide, N-octyl acrylamide, N,N-dialkyl acrylamides, N-methyl acrylamide, N-ethyl acrylamide, N-isopropyl acrylamide, tert-octyl acrylamide, N,N-dimethyl acrylamide, N,N-diethyl acrylamide, N,N-dipropyl acrylamide, N,N-dibutyl acrylamide; and any combinations or mixtures thereof.

Item 25 is a curable precursor according to item 24, wherein the optional co-monomer having an ethylenically unsaturated group is selected to be N-vinyl caprolactam.

Item 26 is a curable precursor according to any of the preceding items, wherein the (co)polymerizable material comprises:
 a) from 60 to 100 parts by weight, from 65 to 95 parts by weight, or even from 65 to 80 parts by weight, of a (meth)acrylate ester monomer; and
 b) optionally, from 0 to 40 parts by weight, from 5 to 35 parts by weight, or even from 20 to 35 parts by weight, of a co-monomer having an ethylenically unsaturated group.

Item 27 is a curable precursor according to any of the preceding items, wherein the (co)polymerizable material comprises a second co-monomer having an ethylenically unsaturated group, which is preferably selected from the group consisting of high Tg monomers.

Item 28 is a curable precursor according to item 27, wherein the high Tg monomer is selected from the group consisting of t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, propyl methacrylate, and any combinations or mixtures thereof.

Item 29 is a curable precursor according to item 27 or 28, wherein the (co)polymerizable material comprises:
 a) from 50 to 100 parts by weight, from 60 to 90 parts by weight, or even from 65 to 80 parts by weight, of a (meth)acrylate ester monomer; and
 b) optionally, from 0 to 20 parts by weight, from 5 to 15 parts by weight, or even from 5 to 10 parts by weight, of a co-monomer having an ethylenically unsaturated group; and
 c) optionally, from 0 to 30 parts by weight, from 5 to 25 parts by weight, or even from 15 to 25 parts by weight, of a second co-monomer having an ethylenically unsaturated group.

Item 30 is a curable precursor according to any of the preceding items, wherein the (co)polymeric material comprising the reaction product of a (co)polymerizable material comprising a (meth)acrylate ester monomer, is free of acid functional monomers.

Item 31 is a curable precursor according to any of the preceding items, which further comprises a filler material which is preferably selected from the group consisting of filler particles, in particular expanded perlite, microspheres, expendable microspheres, glassbeads, glass microspheres, silica type fillers, hydrophobic silica type fillers, hydrophilic silica type fillers, hydrophobic fumed silica, hydrophilic fumed silica, fibers, electrically and/or thermally conducting particles, nanoparticles, in particular silica nanoparticles, and any combinations or mixtures thereof.

Item 32 is a curable precursor according to item 31, wherein the particulate filler material comprises hollow glass microspheres.

Item 33 is a curable precursor according to any of the preceding items, comprising:
 a) 100 parts by weight of a (co)polymeric material comprising the reaction product of a (co)polymerizable material comprising a (meth)acrylate ester monomer; and optionally, a co-monomer having an ethylenically unsaturated group;
 b) from 0.1 to 30 parts by weight, from 0.5 to 25 parts by weight, from 1 to 20 parts by weight, from 1 to 15 parts by weight, or even from 5 to 15 parts by weight, of a polyfunctional aziridine curing agent;
 c) from 0.01 to 10 parts by weight, from 0.1 to 8 parts by weight, from 0.2 to 6 parts by weight, or even from 0.2 to 5 parts by weight, of an acid generating agent; and
 d) optionally, from 1 to 20 parts by weight, from 3 to 15 parts by weight, or even from 5 to 13 parts by weight, of a filler material, preferably hollow glass microspheres.

Item 34 is a cured pressure sensitive adhesive obtainable by curing the curable precursor according to any of the preceding items, wherein the curing step is preferably performed by allowing acid to be released into the curable precursor of a pressure sensitive adhesive.

Item 35 is a cured pressure sensitive adhesive according to item 34, wherein the curing step is performed by subjecting the curable precursor of a pressure sensitive adhesive to a triggering energy sufficient to allow the acid generating agent to release acid into the curable precursor of a pressure sensitive adhesive, and wherein the triggering energy is preferably selected from the group of thermal energy or actinic radiation, more preferably UV radiation.

Item 36 is a composite assembly comprising a substrate and a curable precursor of a pressure sensitive adhesive according to any of items 1 to 33 applied onto at least part of the surface of the substrate, thereby forming a layer of a curable precursor of a pressure sensitive adhesive.

Item 37 is a composite assembly according to item 36, wherein the layer of a curable precursor of a pressure sensitive adhesive is cured, preferably by allowing acid to be released into the curable precursor of a pressure sensitive adhesive.

Item 38 is a composite assembly according to item 37, wherein the curing step is performed by subjecting the curable precursor of a pressure sensitive adhesive to a triggering energy sufficient to allow the acid generating agent to release acid into the curable precursor of a pressure sensitive adhesive, and wherein the triggering energy is preferably selected from the group of thermal energy or actinic radiation, more preferably UV radiation.

Item 39 is a composite assembly according to any of items 36 to 38, wherein the layer of a curable precursor of a pressure sensitive adhesive takes the form of a polymeric foam layer.

Item 40 is a composite assembly according to any of items 36 to 39, which is an adhesive article, and wherein the substrate is preferably a flexible backing layer.

Item 41 is a (post) curing system for pressure sensitive adhesives, comprising a polyfunctional aziridine curing agent and an acid generating agent.

Item 42 is a method of applying a pressure sensitive adhesive to a substrate, comprising the steps of:
a) providing a curable precursor of a pressure sensitive adhesive comprising:
  i. a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
  ii. a polyfunctional aziridine curing agent; and
  iii. optionally, an acid generating agent;
b) applying the curable precursor of a pressure sensitive adhesive to at least part of the surface of the substrate; and
c) curing the curable precursor of a pressure sensitive adhesive by allowing acid to be released into it.

Item 43 is a method of applying a pressure sensitive adhesive to a substrate, comprising the steps of:
a) providing a curable precursor of a pressure sensitive adhesive comprising:
  i. a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
  ii. a polyfunctional aziridine curing agent; and
  iii. optionally, an acid generating agent;
b) partially curing the curable precursor of a pressure sensitive adhesive by allowing acid to be released into it;
c) applying the partially cured pressure sensitive adhesive to at least part of the surface of the substrate; and
d) allowing the partially cured pressure sensitive adhesive to fully cure onto the substrate.

Item 44 is a method according to item 42 or 43, whereby the curing step is performed by subjecting the curable precursor of a pressure sensitive adhesive to a triggering energy sufficient to allow the acid generating agent to release acid into the curable precursor of a pressure sensitive adhesive, and wherein the triggering energy is preferably selected from the group of thermal energy or actinic radiation, more preferably UV radiation.

Item 45 is a method according to item 42 or 43, whereby the curing step is performed by contacting the curable precursor of a pressure sensitive adhesive with a source of acid, which is preferably selected from the group consisting of acid-containing compositions, acid-containing layers, acid-containing priming compositions, and any combinations or mixtures thereof.

Item 46 is a method of preparing a cured pressure sensitive adhesive, comprising the steps of:
a) providing a curable precursor of a pressure sensitive adhesive comprising:
  iv. a (co)polymeric material comprising the reaction product of a (co)polymerizable material comprising a (meth)acrylate ester monomer; and optionally, a co-monomer having an ethylenically unsaturated group and which is different from the (meth)acrylate ester monomer;
  v. a polyfunctional aziridine curing agent; and
  vi. optionally, an acid generating agent; and
b) curing the curable precursor of a pressure sensitive adhesive by allowing acid to be released into it.

Item 47 is a method according to item 46, whereby the curing step is performed by subjecting the curable precursor of a pressure sensitive adhesive to a triggering energy sufficient to allow the acid generating agent to release acid into the curable precursor of a pressure sensitive adhesive, and wherein the triggering energy is preferably selected from the group of thermal energy or actinic radiation, more preferably UV radiation.

Item 48 is a method according to item 46, whereby the curing step is performed by contacting the curable precursor of a pressure sensitive adhesive with a source of acid, which is preferably selected from the group consisting of acid-containing compositions, acid-containing layers, acid-containing priming compositions, and any combinations or mixtures thereof.

Item 49 is the use of a curable precursor of a pressure sensitive adhesive according to any of items 1 to 30 or the cured pressure sensitive adhesive according to item 31 or 32, for the bonding to an uneven or irregular substrate.

Item 50 is the use of a curable precursor of a pressure sensitive adhesive according to any of items 1 to 30 or the cured pressure sensitive adhesive according to item 31 or 32, for the bonding to a low surface energy substrate.

Item 51 is the use of a combination of a polyfunctional aziridine curing agent and an acid generating agent for preparing a cured pressure sensitive adhesive comprising:
a) a (co)polymeric material comprising the reaction product of a (co)polymerizable material comprising a (meth)acrylate ester monomer; and
b) optionally, a co-monomer having an ethylenically unsaturated group and which is different from the (meth)acrylate ester monomer.

Item 52 is the use of a curable precursor of a pressure sensitive adhesive according to any of items 1 to 30 or the cured pressure sensitive adhesive according to item 31 or 32, for industrial applications, in particular for construction applications and automotive applications, in particular for taped seal on body applications for the automotive industry.

EXAMPLES

The invention is further illustrated by the following examples. These examples are merely for illustrative purposes only and are not meant to be limiting on the scope of the appended claims.

Test Methods Applied:
90°-Peel-Test at 300 mm/Min (According to Test Method, Finat No. 2):

Pressure sensitive adhesive assembly strips according to the present invention and having a width of 10 mm and a length >175 mm are cut out in the machine direction from the sample material.

For test sample preparation, the liner is first removed from the one adhesive side and placed on an aluminum strip having the following dimension 22×1.6 cm. Then, the adhesive coated side of each PSA assembly strip is placed, after the liner is removed, with its adhesive side down on a clean test panel using light finger pressure. Next, the test samples are rolled twice in each direction with a standard FINAT test roller (weight 6.8 kg) at a speed of approximately 10 mm per second to obtain intimate contact between the adhesive mass and the surface. After applying the pressure sensitive adhesive assembly strips to the test panel, the test samples are allowed to dwell 24 hours at ambient room temperature (23° C.+/−2° C., 50% relative humidity+/−5%) prior to testing. Half of the samples are then submitted to peel testing (uncured version) whilst the other half of the samples are placed in an oven for 20 minutes at 110° C. (cured samples). After sample removal from the oven, the samples are allowed to cool down for a period of 24 hours at ambient room temperature (23° C.+/−2° C., 50% relative humidity+/−5%).

For peel testing, the test samples are in a first step clamped in the lower movable jaw of a Zwick tensile tester (Model Z020 commercially available from Zwick/Roell GmbH, Ulm, Germany). The pressure sensitive adhesive film strips are folded back at an angle of 90° and their free ends grasped in the upper jaw of the tensile tester in a configuration commonly utilized for 90° peel measurements. The tensile tester is set at 300 mm per minute jaw separation rate. Test results are expressed in Newton per 10 mm (N/10 mm). The quoted peel values are the average of two 90°-peel measurements.

Tensile Testing Using T-Block Geometry at 100 m/Min

The test is carried out at ambient room temperature (23° C.+/−2° C.) and 50%+/−5% relative humidity. First, the aluminum T-Block surface is roughened with a ScotchBrite 4774 cleaning sponge and afterwards cleaned with pure isopropyl alcohol. The cleaned aluminum T-Block test surface is then further pre-treated with a commercially available 3M Primer P94 to avoid pop-off aluminum failures during testing. The liner is first removed from one side of the test specimen. A first aluminum T-Block is then brought onto the exposed adhesive surface of the test specimen and the overstanding adhesive is cut at the edges of the aluminum T-Block. The liner on the other side of the test specimen is thereafter removed and a second, in the same way cleaned and primed aluminum T-Block is brought then onto the open adhesive surface and overstanding edges cut off. A force of 300 N+/−5 N for 15 seconds is then applied onto the prepared test sample. After a dwell time of at least 24 hours at ambient room temperature (23° C.+/−2° C. and 55%+/−5% relative humidity) the test sample is tested in a Zwick tensile tester by performing a tensile test at 100 mm/min. The complete stress-strain curves as well as the adhesion energy and maximal forces are then collected.

Tensile Testing in OLS (Overlap Shear) Geometry at 100 m/Min (in Accordance with ASTMD897)

Overlap shear strength is determined according to ASTM D897 using a tensile tester of the type ZWICK/ROELL Z020 (available from Zwick GmbH & Co. KG, Ulm, Germany) at a crosshead speed of 100 mm/min.

For the test assembly preparation, two aluminium test panels (as later described under point c.), are joined in a overlap connection of 10 mm width and 25 mm length using pressure sensitive adhesive assemblies of the current invention and by pressing these overlap shear test assemblies for 15 seconds with 300N (+/−5N). The test assemblies are then conditioned prior to testing for 24 hours at 23° C.+/−2° C. and 50%+/−5% relative humidity.

Test Panels/Substrates Used for Testing:

a.) Stainless steel test panels according to EN1939:20, surface 1.4301 mirror-like (commercially available from Rocholl GmbH) having a dimension of 150 mm×50 mm×2 mm are the selected panels for all 90° peel tests.

Prior to testing the stainless steel panels are cleaned according to the following described procedure. First, the stainless steel panels are wiped once with heptane, then with MEK followed by a last wipe with heptane and thereafter dried with a paper tissue.

b.) Aluminum T-Blocks: $AlMg_3$ (Int. 5754) T-Profile, dimension of 25 mm×25 mm and a height of 25 mm with 10 mm wide drilled hole; material thickness 3 mm.

The aluminium T-Blocks are cleaned as follows. First, the aluminum T-Block surface is roughened with a ScotchBrite 4774 sponge (commercially available by 3M Deutschland GmbH, Germany) and then cleaned with pure isopropyl alcohol. The cleaned aluminum T-Block test surface is further pretreated with a commercially available 3M Primer P94.

c.) Aluminum test panels in accordance with ASTM B211 having a dimension of 50 mm×25 mm×1 mm. Prior to the preparation of an OLS test assembly, the aluminium panels are roughened using ScotchBrite 4774 (commercially available by 3M) and afterwards wiped once with isopropyl alcohol. Drying is done using a paper tissue. The cleaned aluminum test panel surface is then further pretreated with a commercially available 3M Primer P94.

Raw Materials:

In the examples, the following raw materials are used:

2-Ethyl hexyl acrylate ($C_8$-acrylate, 2-EHA): is an ester of 2-ethylalcohol and acrylic acid which is obtained from BASF AG, Germany. Tg value: −58° C.

N-Vinyl caprolactam (NVC): monofunctional acrylic monomer with an amide-group in the side-chain, commercially available from BASF GmbH, Ludwigshafen, Germany.

Irgacure 651: 2.2-Dimethoxy-1,2-diphenylethan-1-one is an initiator for radical polymerization, commercially available from BASF GmbH, Ludwigshafen, Germany.

K-Pure CXC-1612: Quarternary amine blocked SbF6, thermal acid generator, commercially available by King Industries Inc., Norwalk, U.S.A.

K-Pure CXC-1614: Quarternary amine blocked triflic acid, thermal acid generator, commercially available by King Industries Inc., Norwalk, U.S.A.

K-Pure CXC-1802: Quarternary amine blocked superacid similar to CXC-1612 but without antimony, thermal acid generator, commercially available by King Industries Inc., Norwalk, U.S.A.

Irgacure PAG 290: tetralis (2,3,4,5,6-pentafluorophenyl) boranide; tris(4-(4-acetylphenyl)sulfonylphenyl) sulfonium, photo acid generator, commercially available from BASF GmbH, Ludwigshafen, Germany.

Aziridine curing agent A: CX-100 Trimethylolpropane tris (2-methyl-1-aziridinepropionate), trifunctional aziridine curing agent, commercially available from DSM Neo Resins BV, Waalwijk, Netherlands.

Aziridine curing agent C: Ethoxylated (4 EO) Bisphenol A Bis[3-(2-Methyaziridino)-propanoate]

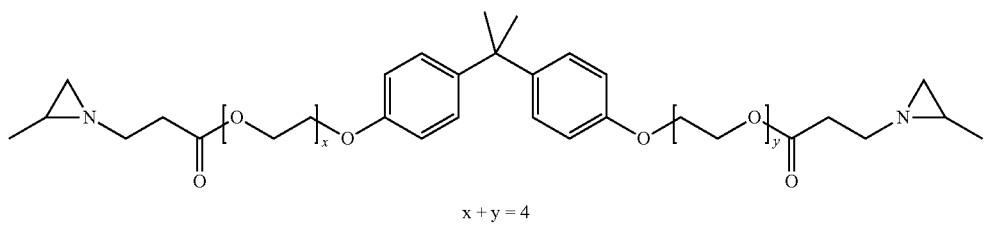

x + y = 4 synthesized as later described.
Aziridine curing agent B: Ethoxylated (14 EO) Trimethylolpropane Tris[3-(2-Methyaziridino)-propanoate]

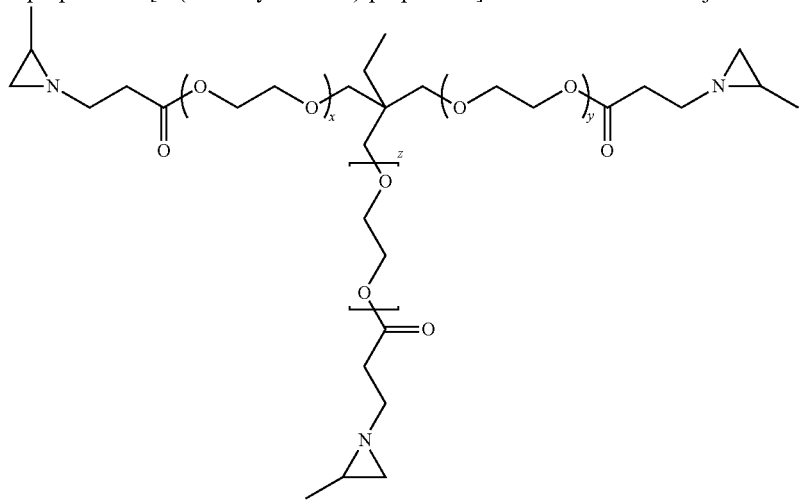

wherein x+y+z=14, and synthesized as later described.
Aziridine curing agent D: (2-(2-Methyl-acryloxy)-ethyl-carbamato)-Pentaerythritol Tris[3-(2-Methyaziridino)-propanoate]

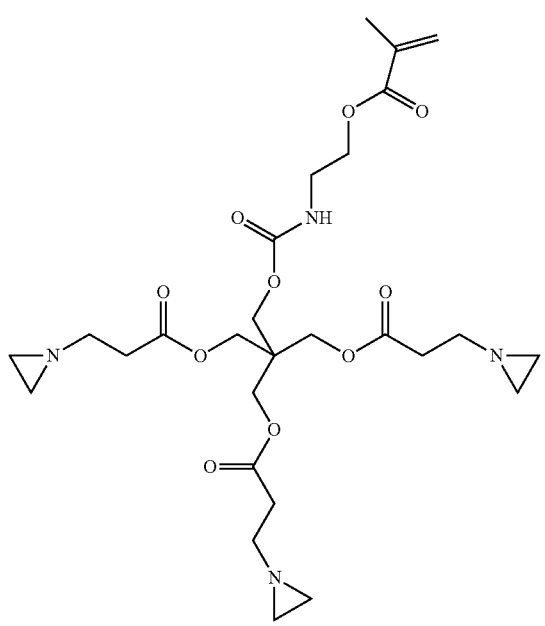 [SMILES: C=C(C)C(=O)OCCNC(=O)OCC(COC(=O)CCN1CC1)(COC(=O)CCN1CC1)COC(=O)CCN1CC1]

synthesized as later described.

Omnirad BDK: 2,2-dimethoxy-2-phenylacetophenone is a UV-initiator, commercially available from iGm resins, Waalwijk Netherlands.

3M Glass bubbles (K15) are hollow glass bubbles with a diameter of 115 m, available from 3M, Germany.
3M Glass bubbles (K37) are hollow glass bubbles with a diameter of 85 μm, available from 3M, Germany.
Aerosil R-972 are hydrophobic fumed silica particles, available from Evonik, Germany.
Calcium Oxide: stabilizer, commercially available from Sigma Aldrich, Seelze, Germany.
Primer 94 (P94): adhesion promoter for pressure sensitive adhesives to surfaces such as polyethylene, polypropylene, ABS, PET/PBT blends, concrete, wood, glass, metal and painted metal surfaces, commercially available from 3M Deutschland GmbH, Germany.
Preparation of Aziridine Curing Agent B:
In a round bottom flask, 1,1,1-Trishydroxymethylpropane-ethoxylate (~14 EO/3OH) triacrylate (200 g=658 meq. C=C, e.g. Sartomer SR9035) is placed. 2.14 g equaling 3 ml triethyl amine are added and the mixture is stirred. To the clear solution, 2-methyl aziridine (137.5 g=2408.4 mmol) is then added dropwise at ambient room temperature (23° C.+/−2° C.) and 50%+/−5% relative humidity while continuously stirring. The temperature initially remains at 23 to 24° C. but rises to about 41° C. after about 30% of the addition of 2-methyl aziridine. In order to keep the temperature of reaction mixture at 35 to 40° C., an ice bath is used. Entire dosing time is about 2 hours. After that, the reaction mixture is stirred 96 hours at ambient room temperature to ensure that there are no more traces of acrylate double bonds visible in the $^1$H NMR spectrum of the reaction mixture. Excess 2-methyl aziridine together with triethyl amine are removed by vacuum distillation at 40° C. and 0.1 mbar. A clear yellow oil in a yield of 97% (229 g) is obtained with a kinematic viscosity of 24.9 mPa*s at 23° C. and 50-100 l/s.
Preparation of Aziridine Curing Agent C:

In a round bottom flask, ethoxylated (4EO) bisphenol A diacrylate (500 g=1927 meq. C=C, e.g. Sartomer SR601E) is placed. 6.25 g equaling 8.6 ml triethyl amine are then added and the mixture is stirred. To the clear solution 2-methyl aziridine (137.5 g=2408.4 mmol) are added dropwise at ambient room temperature (23° C.+/−2° C.) and 50%+/−5% relative humidity while continuous stirring. The temperature initially remains at 23° C. to 24° C. but rises to about 41° C. after about 20% of addition of 2-methyl aziridine. In order to keep the temperature of reaction mixture at 35° C. to 40° C., an ice bath is used. The entire dosing time is approximately 4 hours. After that, the reaction mixture is stirred 48 hours at ambient room temperature. After that time, no more traces of acrylate double bonds are visible in the $^1$H NMR spectrum of the reaction mixture. Excess 2-methyl aziridine together with triethyl amine are then removed by vacuum distillation at 40° C. and 0.1 mbar. A clear colorless oil in a yield of 99% (602 g) is obtained with a kinematic viscosity of 1.5 Pa*s at 23° C. and 50-100 l/s.

Preparation of aziridine curing agent D:

In a round bottom flask, 0.0800 g bismuth neodecanoate, 0.0068 g 4-methoxy phenol, 0.0068 g BHT (2,6-Di-tert-butyl-p-cresole) and 50.0 g equaling 117 mmole PZ-33 (PolyAziridine, LLC—PO Box 637-Medford, N.J. 08055) (CAS-#57116-45-7) are charged. The mixture is stirred until the solid components are dissolved. Subsequently, 13.7 g equaling 88 mmole isocyanatoethyl methacrylate are added dropwise. The temperature of the reaction mixture is kept below 35° C. using an ice bath. The addition of the isocyanatoethyl methacrylate is completed within 15 minutes. Two hours after the addition is completed, no more residual NCO-bands at 2130 cm$^{-1}$ can be detected. A clear, viscous, yellow resin is obtained. Yield is 59 g (87%).

Preparation of the Curable Precursors and Comparative Examples (C1/C2):

The curable precursors of C1, C2 and CP1-CP24 of the pressure sensitive adhesives, are prepared by combining the C8 acrylate (2-EHA) and 0.04 pph of Omnirad BDK as a photoinitiator in a glass vessel. Before the UV exposure is initiated, the mixture is flushed 10 minutes with nitrogen and nitrogen is also bubbled into the mixture the whole time until the polymerization process is stopped by adding air to the syrup. All the time, the mixture is stirred with a propeller stirrer (300 U/min) and the reaction is stopped when a viscosity around 4500 mPas is reached (when measured with a Brookfield viscosimeter, T=25° C., spindle 4, 12 rpm). Additionally, the remaining amount of 0.16 pph Omnirad BDK, the selected aziridine curing agent, the selected glass bubbles or mixtures thereof and part of the NVC (10 g of NVC are put aside) are added to the syrup and mixed until they have dissolved/dispersed. Finally, the initiator-dissolved in the residual 10 g NVC—is added under continuous stirring. The exact formulations of the curable precursors are later listed (in pph) in Tables 2 to 4 below.

For coating the curable precursors, the line speed of the coater is set to 0.82 m/min. The resulting adhesive layer thickness is about 800 μm. Curing is accomplished in a UV-curing station with a length of 300 cm at the line speed given above. The total radiation intensity irradiated cumulatively from top and bottom and the respective length of the three coating zones within the UV-curing station are as follows:

TABLE 1

|  | Zone 1 | Zone 2 | Zone 3 |
|---|---|---|---|
| Total intensity [mW/cm$^2$] | 2.07 | 4.27 | 4.98 |

Formulations of the Curable Precursors Used for Making the Pressure Sensitive Adhesives The formulations of the curable precursors used for making the pressure sensitive adhesives are listed in Tables 2, 3 and 4 below. Table 2 contains comparative examples 1 and 2, later referred to as C1 and C2, which are curable precursors without acid generating agent and without polyfunctional aziridine curing agent. Curable precursors listed in Table 2 have different thermal acid generators and/or varying amounts of a co-monomer having an ethylenically unsaturated group.

TABLE 2

| Curable precursor (CP) | 2-EHA w % | NVC w % | BDK I pph | BDK II pph | CXC-1612 pph | CXC-1614 pph | CXC-1802 pph | CX 100 pph | GBK15 pph |
|---|---|---|---|---|---|---|---|---|---|
| C1 | 75 | 25 | 0.04 | 0.16 | — | — | — | — | 9 |
| C2 | 75 | 25 | 0.04 | 0.16 | — | — | — | 5 | 9 |
| CP1 | 70 | 30 | 0.04 | 0.16 | 0.6 | — | — | 5 | 9 |
| CP2 | 75 | 25 | 0.04 | 0.16 | 0.6 | — | — | 5 | 9 |
| CP3 | 70 | 30 | 0.04 | 0.16 | — | 0.6 | — | 5 | 9 |
| CP4 | 75 | 25 | 0.04 | 0.16 | — | 0.6 | — | 5 | 9 |
| CP5 | 70 | 30 | 0.04 | 0.16 | — | — | 0.6 | 5 | 9 |
| CP6 | 75 | 25 | 0.04 | 0.16 | — | — | 0.6 | 5 | 9 |
| CP7 | 70 | 30 | 0.04 | 0.16 | — | 0.6 | — | 10 | 9 |
| CP8 | 70 | 30 | 0.04 | 0.16 | — | 0.6 | — | 5 | 9 |
| CP9 | 70 | 30 | 0.04 | 0.16 | — | 0.6 | — | 1 | 9 |

Curable precursors listed in Table 3 use different kinds of polyfunctional aziridine curing agents.

TABLE 3

| | Monomer | | Initiator | | | Aziridine | | | | Filler |
|---|---|---|---|---|---|---|---|---|---|---|
| Curable precursor | 2-EHA w % | NVC w % | BDK I pph | BDK II pph | CXC-1614 pph | A pph | B pph | C pph | D pph | GBK15 pph |
| CP10 | 75 | 25 | 0.04 | 0.16 | 0.6 | — | 10 | — | — | 9 |
| CP11 | 75 | 25 | 0.04 | 0.16 | 0.6 | — | 5 | — | — | 9 |
| CP12 | 75 | 25 | 0.04 | 0.16 | 0.6 | — | 1 | — | — | 9 |
| CP13 | 75 | 25 | 0.04 | 0.16 | 0.6 | — | — | 10 | — | 9 |
| CP14 | 75 | 25 | 0.04 | 0.16 | 0.6 | — | — | 5 | — | 9 |
| CP15 | 75 | 25 | 0.04 | 0.16 | 0.6 | — | — | 1 | — | 9 |
| CP16 | 75 | 25 | 0.04 | 0.16 | 0.6 | 4 | — | — | 1 | 9 |

TABLE 3-continued

| | Monomer | | Initiator | | | Aziridine | | | Filler |
| | | | BDK | BDK | CXC- | | | | |
| | 2-EHA | NVC | I | II | 1614 | A | B | C | D | GBK15 |
| Curable precursor | w % | w % | pph | pph | pph | pph | pph | pph | pph | pph |
|---|---|---|---|---|---|---|---|---|---|---|
| CP17 | 75 | 25 | 0.04 | 0.16 | 0.6 | — | 4 | — | 1 | 9 |
| CP18 | 75 | 25 | 0.04 | 0.16 | 0.6 | — | — | 4 | 1 | 9 |

Table 4 below provides the formulations of curable precursors having different kinds of aziridines, a photo acid generating agent ("Photo Acid Generating agent") and which are coated by either a solvent-based or a Hot Melt process.

TABLE 4

| | Monomer | | Initiator | | Aziridine | | PAG | Fillers | | |
| | 2- | | BDK | BDK | | | Irgacure | | Aerosil | |
| Curable precursor | EHA w % | NVC w % | I pph | II pph | 1 pph | 2 pph | 290 pph | GBK37 pph | R972 pph | CaO pph |
|---|---|---|---|---|---|---|---|---|---|---|
| CP19 | 70 | 30 | 0.04 | 0.16 | 20 | — | 4 | — | — | — |
| CP20 | 70 | 30 | 0.04 | 0.16 | 20 | — | 4 | — | — | 0.06 |
| CP21 | 70 | 30 | 0.04 | 0.16 | 20 | — | 4 | — | — | 0.60 |
| CP22 | 70 | 30 | 0.04 | 0.16 | — | 10 | — | 10 | 3 | 0.06 |
| CP23 | 70 | 30 | 0.04 | 0.16 | — | 10 | 2 | 10 | 3 | 0.06 |
| CP24 | 70 | 30 | 0.04 | 0.16 | — | 10 | 4 | 10 | 3 | 0.06 |

Test Results:
90° Peel Results on Stainless Steel Panels

The peel results of comparative examples C1 and C2, as well as of the pressure sensitive adhesives made from curable precursors CP1-CP9 are shown in Table 5 below.

TABLE 5

| Curable precursor used | Peel value (N/cm), (uncured) | Peel value (N/cm), (cured 20 min at 110° C.) | Peel value (N/cm), (cured on substrate for 20 min at 110° C.) |
|---|---|---|---|
| C1 | 13.9 | 10.6 | 11.4 |
| C2 | 8.9 | 10.3 | 7.7 |
| CP1 | 12.7 | 10.7 | 20.4 |
| CP2 | 14.4 | 10.0 | 35.7 |
| CP3 | 13.0 | 12.1 | 22.1 |
| CP4 | 14.4 | 12.9 | 30.2 |
| CP5 | 13.7 | 11.1 | 32.1 |
| CP6 | 11.9 | 10.8 | 26.4 |
| CP7 | 9.7 | 9.2 | 17.8 |
| CP8 | 13.0 | 12.1 | 22.1 |
| CP9 | 16.2 | 12.9 | 18.7 |

Comparative examples C1 and C2 show no increase in peel behavior after curing, whereas the pressure sensitive adhesives made from curable precursors according to the invention (C1-C9) show surprisingly strong increases in their peel performance after being cured on a substrate. This is applicable to all thermal acid generating agents used.

OLS and T-Block Tensile Results

The results of the OLS tensile testing for the pressure sensitive adhesives made from curable precursors CP1-CP9, as well as comparative examples C1 and C2 are provided in Table 6. In this table, the resulting forces at 2 mm and 4 mm elongation for uncured and cured pressure sensitive adhesives are listed.

TABLE 6

| Curable precursor used | F (2 mm)/N (uncured) | F (2 mm)/N (cured 20 min at 110° C.) | F (4 mm)/N (uncured) | F (4 mm)/N (cured 20 min at 110° C.) |
|---|---|---|---|---|
| C1 | 74.2 | 64.9 | 111.1 | 96.2 |
| C2 | 53.6 | 55.5 | 100.2 | 96.4 |
| CP1 | 203.2 | 263.0 | 356.8 | 512.3 |
| CP2 | 86.7 | 162.6 | 148.4 | 362.4 |
| CP3 | 109.7 | 149.7 | 186.2 | 308.7 |
| CP4 | 78.4 | 107.2 | 126.1 | 212.3 |
| CP5 | 123.1 | 192.8 | 217.3 | 396.5 |
| CP6 | 71.3 | 116.2 | 138.8 | 261.2 |
| CP7 | 81.7 | 163.4 | 132.1 | 340.7 |
| CP8 | 109.7 | 149.7 | 186.2 | 308.7 |
| CP9 | 179.0 | 181.7 | 304.1 | 355.1 |

Tensile testing in OLS geometry shows for C1 and C2 no curing effect after being treated with 110° C. for 20 minutes. For the pressure sensitive adhesives made from curable precursors according to the invention (CP1-CP9), the post-curing effect of the pressure-sensitive adhesives can be clearly seen, irrespective of which thermal acid generating agent is selected.

The results of the T-block tensile testing for the pressure sensitive adhesives made from curable precursors CP1-CP9, as well as comparative examples C1 and C2 are provided in Table 7. In this table, the resulting forces at 2 mm and 4 mm elongation of cured and uncured pressure sensitive adhesives are listed.

TABLE 7

| Curable precursor used | F (2 mm)/N (uncured) | F (2 mm)/N (cured 20 min at 110° C.) | F (4 mm)/N (uncured) | F (4 mm)/N (cured 20 min at 110° C.) |
|---|---|---|---|---|
| C1  | 218.6 | 224.1 | 222.22 | 231.9 |
| C2  | 170.1 | 201.7 | 178.1  | 237.3 |
| CP1 | 487.8 | 835.7 | 150.6  | —     |
| CP2 | 262.4 | —     | 270.1  | —     |
| CP3 | 292.8 | 613.6 | 308.7  | 356.6 |
| CP4 | 221.6 | 437.0 | 228.6  | 275.1 |
| CP5 | 421.9 | 560.8 | 347.6  | 588.2 |
| CP6 | 283.1 | 442.7 | 371.9  | —     |
| CP7 | 241.1 | 678.8 | 269.4  | —     |
| CP8 | 292.8 | 630.4 | 308.7  | 252.2 |
| CP9 | 423.9 | 632.3 | 398.9  | 683.3 |

Similar to the results in Table 6, the results of the mechanical tensile testing in T-block geometry also clearly show the post-curing effects of the pressure sensitive adhesives when compared to comparative examples C1 and C2.

The results of the OLS tensile testing for the pressure sensitive adhesives made from curable precursors CP10-CP18 are provided in Table 8. In this table, the resulting forces at 2 mm and 4 mm elongation for uncured and cured pressure sensitive adhesives are listed. These pressure sensitive adhesives have in common that they all have the same thermal acid generating agent but use different polyfunctional aziridine curing agents in varying amounts.

TABLE 8

| Curable precursor used | F (2 mm)/N (uncured) | F (2 mm)/N (cured 20 min at 110° C.) | F (4 mm)/N (uncured) | F (4 mm)/N (cured 20 min at 110° C.) |
|---|---|---|---|---|
| CP10 | 93.7  | 111.0 | 156.1 | 203.6 |
| CP11 | 89.1  | 108.6 | 141.1 | 189.3 |
| CP12 | 101.1 | 120.0 | 160.6 | 211.7 |
| CP13 | 92.9  | 150.6 | 153.0 | 308.8 |
| CP14 | 92.5  | 127.1 | 156.3 | 257.3 |
| CP15 | 95.2  | 128.0 | 155.1 | 247.6 |
| CP16 | 127.5 | 194.1 | 248.8 | 118.7 |
| CP17 | 143.0 | 208.8 | 305.1 | 212.5 |
| CP18 | 123.3 | 227.3 | 267.9 | —     |

The results of the T-block tensile testing for the pressure sensitive adhesives made from curable precursors CP10-CP18 are provided in Table 9. In the table, the resulting forces at 2 mm and 4 mm elongation of cured and uncured pressure sensitive adhesives are listed.

TABLE 9

| Curable precursor used | F (2 mm)/N (uncured) | F (2 mm)/N (cured 20 min at 110° C.) | F (4 mm)/N (uncured) | F (4 mm)/N (cured 20 min at 110° C.) |
|---|---|---|---|---|
| C10  | 254.4 | 422.9 | 319.1 | 543.94 |
| C11  | 234.6 | 300.6 | 274.8 | 359.8  |
| CP12 | 229.4 | 403.2 | 246.8 | 441.2  |
| CP13 | 292.9 | 566.8 | 319.6 | 662.1  |
| CP14 | 256.9 | 549.4 | 273.8 | 357.0  |
| CP15 | 267.0 | 468.5 | 280.3 | 576.7  |
| CP16 | 440.6 | 81.1  | 291.2 | —      |
| CP17 | 392.1 | 265.1 | —     | —      |
| CP18 | 322.9 | 217.2 | —     | —      |

The results of the mechanical tensile testing in OLS and T-Block geometry from Tables 8 and 9 clearly show, that by varying the number of aziridine functionalities, the molecular weight of the selected aziridine curing agent and by modifying the chosen amount of an aziridine curing agent, the properties of post-cured tapes can be modified concerning such properties as elongation at break and forces at break.

The results of the OLS tensile testing for the pressure sensitive adhesives made from curable precursors CP19-CP24 are provided in Table 10. In this table, the resulting forces at 2 mm and 4 mm elongation for uncured and cured pressure sensitive adhesives are listed. The pressure sensitive adhesives made from curable precursors CP19, CP20 and CP21 are made by making a polymer mixture of 2-EHA and NVC as previously described for all prior listed precursors C1-C18. This polymer mixture is then solved in ethyl acetate, in order to prepare a coating solution. The aziridine and the photo acid generating agent are added to a 33% solution of the polymer mixture. A coating thickness of 350 µm is coated onto a siliconized liner (commercially available as Akrosil BR90GGLSILSILOX G1H/G7 Scotchcal from Akrosil Europe) and dried at 80° C. for 10 minutes in an oven. The pressure sensitive adhesive layers obtained this way are then laminated on top of each other 8 times and then pressed to a total thickness of 800 µm with an heatable hydraulic table press (type no. TP400, commercially available by Fortune, Holland) first at a pneumatic pressure of 10 kN for 1 minute at 80° C. followed by 30 minutes at 80° C. using a pneumatic pressure of 40 kN.

The pressure sensitive adhesives made from curable precursors CP22 to CP24 are obtained by making a polymer mixture of 2-EHA and NVC as previously described for all prior listed precursors C1-C18. This polymer mixture is then kneaded at 170° C. at a torque of 60 Nm in a kneader type Plastograph 350EHT (commercially available from Brabender GmbH & Co. KG, Germany) together with fillers, the aziridine and the photo acid generating agent. After that the hot melt mixture is pressed to a thickness of 800 µm using a heatable hydraulic table press (type no. TP400, commercially available by Fortune, Holland) first at a pneumatic pressure of 10 kN at 150° C. followed by 5 minutes at 150° C. with a pneumatic pressure of 40 kN.

Curing of the pressure sensitive adhesives is done using a UV-A lamp, type UVA lamp 250 commercially available from Dr. Honle in Planegg, Germany.

TABLE 10

| Curable precursor used | F (2 mm)/N (uncured) | F (2 mm)/N (cured 30 s UV-A) | F (4 mm)/N (uncured) | F (4 mm)/N (cured 30 s UV-A) |
|---|---|---|---|---|
| C19  | 20.7  | 32.6  | 50.3  | 130.1 |
| C20  | 23.2  | 36.4  | 52.9  | 139.5 |
| CP21 | 22.2  | 35.1  | 49.3  | 136.1 |
| CP22 | 120.1 | 230.1 | 118.7 | 210.3 |
| CP23 | 128.7 | 232.7 | 150.5 | 306.0 |
| CP24 | 152.8 | 274.8 | 219.7 | 384.2 |

The post-curing effect increases with an increasing amount of the photo acid generating agent and polyfunctional aziridine in the curable precursor and can be seen in the OLS tensile testing of CP22 to CP24.

The invention claimed is:
1. A cured pressure sensitive adhesive comprising a cured product of a curable precursor, wherein the cured product is an interpenetrating polymer network that is formed from a (meth)acrylate ester based (co)polymeric network and an aziridine polymeric network, wherein a) the (meth)acrylate ester based (co)polymeric network comprising the reaction product of a (co)polymerizable material comprising a (meth)acrylate ester monomer;

an optional co-monomer having an ethylenically unsaturated group, the co-monomer being a non-acid functional polar monomer;

b) the aziridine polymeric network resulting from acid-catalyzed cationic ring-opening polymerization of a reaction mixture comprising a polyfunctional aziridine having at least two aziridine functional groups; and an acid generating agent selected from the group consisting of thermal acid generating agents, photo acid generating agents, and any combinations or mixtures thereof.

2. The cured pressure sensitive adhesive of claim 1, wherein the polyfunctional aziridine has the following formula:

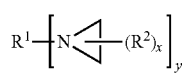
(I)

wherein $R^1$ is a (hetero)hydrocarbyl group;

$R^2$ is an H, $C_1$-$C_{12}$ alkyl group, or $C_6$-$C_{12}$ aromatic group;

x is 0, 1 or 2, and y is at least 2.

3. The cured pressure sensitive adhesive of claim 1, wherein the polyfunctional aziridine curing agent has the following formula:

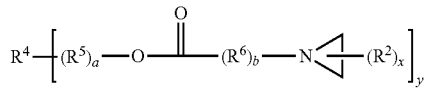
(IV)

wherein $R^4$ is a (hetero)hydrocarbyl group having a valency of y;

$R^5$ and $R^6$ are independently (hetero)hydrocarbyl groups;

$R^2$ is an H, $C_1$-$C_{12}$ alkyl group, or $C_6$-$C_{12}$ aromatic group;

y is at least 2;

x is 0, 1 or 2; and each of a and b are independently 0 to 6.

4. The cured pressure sensitive adhesive of claim 1, wherein the acid generating agent is a thermal acid generating agent selected from the group consisting of quaternary blocked superacids, amine blocked superacids, and any combinations or mixtures thereof.

5. The cured pressure sensitive adhesive of claim 1, wherein the acid generating agent is a photo acid generating agent selected from the group consisting of ionic salts of organometallic complexes, iodonium or sulfonium salts and any combinations or mixtures thereof.

6. The cured pressure sensitive adhesive of claim 1, wherein the non-acid functional polar monomer has a nitrogen-containing group or a salt thereof.

7. The cured pressure sensitive adhesive of claim 6, wherein the nitrogen-containing group is selected from secondary amido groups and tertiary amido groups.

8. The cured pressure sensitive adhesive of claim 1, wherein the optional co-monomer having an ethylenically unsaturated group is selected to be N-vinyl caprolactam.

9. The cured pressure sensitive adhesive of claim 1, wherein the (co)polymerizable material is free of acid functional monomers.

* * * * *